(12) United States Patent
Huang et al.

(10) Patent No.: US 9,878,984 B2
(45) Date of Patent: Jan. 30, 2018

(54) ANTI-CANCER COMPOUNDS

(71) Applicant: NORTHWESTERN UNIVERSITY, Evanston, IL (US)

(72) Inventors: Sui Huang, Chicago, IL (US); John Norton, San Diego, CA (US); Daniel Appella, Rockville, MD (US); Mark Witschi, Davis, CA (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 372 days.

(21) Appl. No.: 14/480,235

(22) Filed: Sep. 8, 2014

(65) Prior Publication Data

US 2014/0378503 A1  Dec. 25, 2014

Related U.S. Application Data

(60) Continuation of application No. 13/853,513, filed on Mar. 29, 2013, now Pat. No. 8,829,025, which is a division of application No. 12/812,114, filed as application No. PCT/US2009/030757 on Jan. 12, 2009, now Pat. No. 8,420,665.

(60) Provisional application No. 61/020,626, filed on Jan. 11, 2008.

(51) Int. Cl.
  *A61K 31/473* (2006.01)
  *C07D 221/14* (2006.01)
  *A61K 31/43* (2006.01)
  *C07D 217/24* (2006.01)
  *A61K 45/06* (2006.01)

(52) U.S. Cl.
  CPC .......... *C07D 221/14* (2013.01); *A61K 31/43* (2013.01); *A61K 31/473* (2013.01); *A61K 45/06* (2013.01); *C07D 217/24* (2013.01); *A61K 2300/00* (2013.01)

(58) Field of Classification Search
  CPC .................................................. A61K 31/473
  See application file for complete search history.

(56) References Cited

U.S. PATENT DOCUMENTS

| | | |
|---|---|---|
| 5,235,045 A | 8/1993 | Lewis et al. |
| 5,461,176 A | 10/1995 | Sun et al. |
| 5,561,042 A | 10/1996 | Weis et al. |
| 5,616,589 A | 4/1997 | Keilhauer et al. |
| 6,403,604 B1 | 6/2002 | Yang et al. |
| 2003/0032624 A1 | 2/2003 | Yang |
| 2006/0182751 A1 | 8/2006 | Gazzard et al. |
| 2006/0211648 A1* | 9/2006 | Brown ............... A61K 31/4745 514/50 |

FOREIGN PATENT DOCUMENTS

| | | |
|---|---|---|
| EP | 0506008 | 9/1992 |
| WO | 94/06771 | 3/1994 |
| WO | 95/05365 | 2/1995 |
| WO | 00/01672 | 1/2000 |
| WO | 02/054067 | 7/2002 |
| WO | 06/60533 | 6/2006 |

OTHER PUBLICATIONS

VanQuaquebeke et al. ("2,2,2-Trichloro-N-({2-[2-(dimethylamino)ethyl]-1,3-dioxo-2,3-dihydro-1H-benzo[de]isoquinolin-5-yl}carbamoyl)acetamide (UNBS3157), a Novel Nonhematotoxic Naphthalimide Derivative with Potent Antitumor Activity" J. Med. Chem. 2007, 50, 4122-4134).*
National Cancer Institute's Surveillance, Epidemiology and End Results (SEER) Program accessed via https://training.seer.cancer.gov/disease/categories/classification.html on Apr. 24, 2017, 3 pages.*
Ahn, Jinwoo, et al., "The Chk2 protein kinase", Review, DNA Repair 3 (2004) pp. 1039-1047.
Alexiou, Michael, et al., "Nucleophilic Displacement of the Nitro Group in 2- and 4-Nitronaphthalic-1, 8-Anhydrides and Their Derivaties," Tetrahedron Letters, vol. 22, No. 24, pp. 2303-2306 (1981).
Brana, MF, et al., "Bis-naphthalimides. 2. Synthesis and biological activity of 5,6-acenaphthalimidoalkyl-1,8-naphthalimidoalkyl amines," Eur J. Med Chem (1995), 30, pp. 235-239.
Brana, Miguel Fernandez, et al., "Synthesis and cytostatic activity of benz(de)iso-quinolin-1,3-diones. Structure-activity relationships," Eur. J. Med. Chem—Chimica Therapeutica, May-Jun. 1981-16, No. 3, pp. 207-212.
Brana, M F., et al., "Chromophore-Modified Bis-Naphthalimides: Synthesis and Antitumor Activity of Bis-Dibenz[de,h] isoquinoline-1,3-diones", J. Med. Chem. 1997, 40, pp. 449-454.
Brana, Miguel F., et al., "New Analogues of Amonafide and Elinafide, Containing Aromatic Heterocycles: Synthesis, Antitumor Activity, Molecular Modeling, and DNA Binding Properties," J. Med. Chem 2004, 47, pp. 1391-1399.
Brana, M. Fernandez, et al., "Relacion Estructura-Toxicidad Cuantitativa de Benzo[de]Isoquinolein-1,3,Dionas," Anales de Quimica, 1983, vol. 79, pp. 43-46.
Cory, Ann H., et al., "Use of an Aqueous Soluble Tetrazolium/Formazan Assay for Cell Growth Assays in Culture," Cancer Communications, vol. 3, No. 7, 1991, pp. 207-212.
Costanza, Mary E., et al., Amonafide: An Active Agent in the Treatment of Previously Untreated Advanced Breast Cancer—A Cancer and Leukemia Group B Study (CALGB 8642), Clinical Cancer Research, vol. 1, pp. 699-704, Jul. 1995.
Costi, MP, et al., "Naphthalimido derivates as antifolate thymidylate synthase inhibitors," Eur J Med Chem (1996) 31, pp. 1011-1016.

(Continued)

*Primary Examiner* — Kortney L. Klinkel
(74) *Attorney, Agent, or Firm* — Casimir Jones, S.C.

(57) ABSTRACT

The present invention relates to anti-cancer compounds, methods for their discovery, and their therapeutic use. In particular, the present invention provides analogs of the known anti-cancer compound amonafide, and structurally and functionally related compounds, and methods of using such compounds as therapeutic agents to treat a number of conditions associated with hyperproliferation.

3 Claims, 7 Drawing Sheets

(56) References Cited

OTHER PUBLICATIONS

Daffy, Lynda M., et al., "Arenedicarboximide Building Blocks for Fluorescent Photoinduced Electron Transfer pH Sensors Applicable with Different Media and Communication Wavelengths," Chem. Eur. J. 1998, 4, No. 9, pp. 1810-1815.

De Silva, a. Prasanna, et al., "New Fluorescent Model Compounds for the Study of Photoinduced Electron Transfer: The Influence of a Molecular Electric Field in the Excited State," Angew. Chem. Int. Ed. Engl. 1995, 34, No. 16, pp. 1728-1731.

Felder, T.B., et al., "Pharmacokinetics and Metabolism of the Antitumor Drug Amonafide (NSC-308847) in Humans," Drug Metabolism and Disposition, vol. 15, No. 6, pp. 773-778 (1987).

Hsiang, Yaw-Huei, et al., "Topoisomerase II-Mediated DNA Cleavage by Amonafide and Its Structural Analogs," Molecular Pharmacology, 36:371-376, Jun. 7, 1989.

Karmaker, Rana, et al., "Phase-Transfer Catalyst-Induced Changes in the Absorption and Fluorescence Behavior of Some Electron Donor-Acceptor Molecules," J. Am. Chem. Soc. 2001, 123, pp. 3809-3817.

Kawamura, Akane, et al., "Eukaryotic arylamine N-acetyltransferase investigation of substrate specificity by high-throughput screening," Biochemical Pharmacology 69 (2005) pp. 347-359.

Kopp, K., et al., "Perinucleolar Compartment and Transformation," Journal of Cellular Biochemistry 95:217-225 (2005).

Kornek, G., et al., "Amonafide as First-line Chemotherapy for Metastatic Breast Cancer," European Journal of Cancer, 30(4), 398-400 (1994).

Kreis, W., et al., "Clinical Pharmacokinetics of Amonafide (NSC 308847) in 62 Patients," Cancer Investigation, 14(4), 320-327 (1996).

Langlois, M., et al., "Synthesis of quinazoline-2,4-dione and naphthalimide derivatives as new 5-HT3 receptor antagonists," Eur J. Med Chem (1994) 29, pp. 925-940.

Martin, E., et al., "A correlation between redox potentials and photophysical behavior of compounds with intramolecular charge transfer: application to N-substituted 1,8-naphthalimide derivatives," Chemical Physics Letters 288 (1998) 52-58.

Mayr, Craig A., "In vitro cytotoxicity and DNA damage production in Chinese hamster ovary cells and topoisomerase II inhibition by 2-[2'-(dimethylamino)ethyl]-1,2-dihydro-3H-dibenz[de,h]isoquinoline-1,3-diones with substitutions at the 6 and 7 positions (azonafides)," Anti-Cancer Drugs 1997, 8, pp. 245-256.

Mayr, Craig A., et al., "Intracellular localization of 6- and 7-substituted 2-[2'(dimethylamino)ethyl]-1,2-dihydro-3H-dibenz[de,h]isoquinoline-1,3-diones (azonafides) is not the limiting factor for their cytotoxity: an in vitro confocal microscopy study," Anti-Cancer Drugs 1999, 10, pp. 163-170.

Ni, Weijuan, et al., "Synthesis and Luminescent Properties of 2-Phenyl-5-{4[2-(6-substitutent-2H-benz[de] isoquinoline-1,3(2H)-dione-2-yl) polymethanano]amino-}phenyl-1,3,4-oxadiazole," Chemistry Letters 1997, pp. 101-102.

Norton, John T., et al., "Synthesis and anticancer activities of 6-amino amonafide derivatives," Preclinical report. Anti-Cancer Drugs, vol. 19, No. 1 (2008), pp. 24-36.

Pourpak, Alan, et al., "Preclinical antitumor activity, pharmacokinetics and pharmacodynamics of imexon in mice" Anti-Cancer Drugs, vol. 17, No. 10: 1179-1184 (2006).

Ratain, Mark J., et al., "Paradoxical relationship between acetylator phenotype and amonafide toxitcity," Clin. Pharrnacol. Ther., 50: 573-9(1991).

Ratain, Mark J., et al., Population Pharmacodynamic Study of Amonafide: A Cancer and Leukemai Group B Study, Journal of Clinical Oncology, vol. 13, No. 3 (Mar. 1995, pp. 741-747.

Sami, Salah, et al., "Amino-Substituted 2-[2'-(Dimethylamino)ethyl]-1,2-dihydro-3H-dibenz[de,h]isoquinoline-1,3-diones. Synthesis, Antitumor Activity, and Quantitative Structure-Activity Relationship," J. Med. Chem. 1995, 38 pp. 983-993.

Scheithauer, W., et al., "Phase II study of amonafide in advanced breast cancer," Breast Cancer Research and Treatment 20: 63-67 (1991).

Scifinder Scholor, CAS. American Chemical Society, Nov. 11, 2004.

Scifinder Scholar, CAS. American Chemical Society, Nov. 10, 2004.

Desilva, A. Prasanna, et al., "A small supramolecular system which emulates the unidirectional, path-selective photoinduced electron transfer (PET) of the bacterial photosynthetic reaction centre (PRC)", Chem. Commun. 1999 163-164.

Stevenson, Karen A., et al., "A Substituent Constant Analysis of the Interaction of Substituted Naphthalene Monoimides with DNA," J. Med. Chem. 1984, 27, pp. 1677-1682.

Taningher, Maurizio, et al., "Drug metabolism polymorphisms as modulators of cancer susceptibility," Mutation Research 436 (1999) pp. 227-261.

Tian, He, et al., "Synthesis of novel multi-chromophoric soluble perylene derivatives and their photosensitizing properties with wide spectral response for SnO2 nanoporous electrode," J. Mater. Chem. 2000, 10, pp. 2708-2715.

Yuan, Dongwu, et al., "Enhanced Nonradiative Decay in Aqueous Solutions of Aminonaphthalimide Derivatives via Water-Cluster Formation," J. Phys. Chem. A 1997, 101, pp. 3461-3466.

Zhu, Weihong, et al., "Synthesis and Electroluminescence of Novel Copolymers with Charges Transporting Moieties," Chemistry Letters 1999, pp. 501-502.

Andersson et al., 1987, "In vitro toxicity and DNA cleaving capacity of benzisoquinolinedione (nafidimide; NSC 308847) in human leukemia", Cancer Res, vol. 47 pp. 1040-1044.

De Isabella et al., 1995, "Base sequence determinants of amonafide stimulation of topoisomerase II DNA cleavage", Nucleic Acids Res, vol. 23 pp. 223-229.

Dorr et al., 2001, "Preclinical antitumor activity of the azonafide series of anthracene-based DNA intercalators", Anti-Cancer Drugs, 12(3):213-220.

Huang et al., 1997, "The dynamic organization of the perinucleolar compartment in the cell nucleus", J Cell Biol, vol. 137 pp. 965-974.

Stella, Valentino J.,. "Prodrugs as therapeutics" Expert Opinion of Therapeutic Patents (2004) 14(3), pp. 277-280.

Wolff et al., Burger's Medicinal Chemistry, 5th Ed., vol. 1, pp. 975-977 (1994).

Testa, Bernard, "Prodrug Research: futile or fertile?" Biochemical Pharmacology, 200, 68, pp. 2097-2106.

Ettmayer, Peter, "Lessons from Marketed and Investigational Prodrugs", Medicinal Chemistry, 2004, 47(10),2394-2404.

Banthia et al., "Photophysical and transition metal ion signaling properties of some 4-amino-1,8-naphthalimide derivaties," Res. Cehm. Intermed., 2005, 31(1-3), 25-38.

www.xanthus.com/products_xanafide.htm (c) 2006.

www.chemgenex.com/wt/page/quinamed (c) 2011, accessed Jan. 21, 2011.

Wang et al., 2001, "Atp-bound topoisomerase ii as a target for antitumor drugs", J Biol Chem, vol. 276 pp. 15990-15995.

Ratain et al., 1993, "Phase I study of amonafide dosing based on acetylator phenotype", Cancer Res, vol. 53 pp. 2304-2308.

Muller and Mehta, 1988, "DNase I hypersensitivity is independent of endogenous topoisomerase II activity during chicken erythrocyte differentiation", Mol Cell Biol, vol. 8 pp. 3661-3669.

Mayr et al., 1998, "Identification and characterization of in vitro matabolites of 2-2'-(dimethylamino)ethyl-1,2-dihydro-3H-dibenzde, h]isoquinaline-1,3-dione", Drug Metab Dispos, vol. 26 pp. 105-109.

Huang et al., 2008, "Synthesis and anticancer activities of 6-amino amonafide derivatives", Anti-Cancer Drugs, 19 (1):23-36.

Kamath et al., 2005, "Perinucleolar compartment prevalence has an independent prognostic value for breast cancer", Cancer Res, vol. 65 pp. 246-253.

(56) References Cited

OTHER PUBLICATIONS

International Search Report and Written Opinion of the International Searching Authority dated Aug. 20, 2009, International Patent Application No. PCT/US2009/030757, International Filing Date Jan. 12, 2009.

Innocenti et al., 2001, "Pharmacogenetics of anticancer agents: lessons from amonafide and irinotecan", Drug Metab Dispos, vol. 29 pp. 596-600.

* cited by examiner

A.

B.

C.

ANTI-CANCER COMPOUNDS

CROSS-REFERENCE TO RELATED APPLICATIONS

This application is a continuation of pending U.S. patent application Ser. No. 13/853,513, filed Mar. 29, 2013, which will issue on Sep. 9, 2014 as U.S. Pat. No. 8,829,025, which is a divisional of allowed U.S. patent application Ser. No. 12/812,114, filed Aug. 3, 2010, now U.S. Pat. No. 8,420,665, issued Apr. 16, 2013, which is a U.S. 371 national phase entry of expired International Patent Application No. PCT/US2009/030757, international filing date Jan. 12, 2009, which claims priority to expired U.S. Provisional Patent Application No. 61/020,626 filed Jan. 11, 2008, the contents of which are incorporated by reference in their entireties.

FIELD OF THE INVENTION

The present invention relates to anti-cancer compounds, methods for their discovery, and their therapeutic use. In particular, the present invention provides analogs of the known anti-cancer compound amonafide, and structurally and functionally related compounds, and methods of using such compounds as therapeutic agents to treat a number of conditions associated with hyperproliferation.

BACKGROUND

Cancer is a group of diseases in which cells are aggressive (grow and divide without respect to normal limits), invasive (invade and destroy adjacent tissues), and/or metastatic (spread to other locations in the body). These three malignant properties of cancers differentiate them from benign tumors, which are self-limited in their growth and do not invade or metastasize (although some benign tumor types are capable of becoming malignant). Cancer may affect people at all ages, even fetuses, but risk for the more common varieties tends to increase with age. Cancer causes about 13% of all deaths. Improved methods for treating cancer are needed.

SUMMARY OF THE INVENTION

The present invention relates to anti-cancer compounds, methods for their discovery, and their therapeutic use. In particular, the present invention provides analogs of the known anti-cancer compound amonafide, and structurally and functionally related compounds, and methods of using such compounds as therapeutic agents to treat a number of conditions associated with hyperproliferation.

The present invention relates to metabolically stable analogs of a known anti-cancer drug, amonafide. In order to eliminate the metabolic instability of amonafide while retaining the anti-cancer properties nine derivatives that are structurally similar to amonafide that should not be acetylated were synthesized. Eight derivatives have aryl amines at the 6-position (vs. 5-position of amonafide) and one derivative completely lacks the aryl amine. These derivatives can evade metabolism by NAT2, which will hence likely improve the clinical management of patients compared to those treated with amonafide. The analogs reported here may serve as a clinical replacement for amonafide or may be used a novel metabolically stable anti-cancer drugs.

Accordingly, in certain embodiments, the present invention provides compositions comprising a compound described by the following formula:

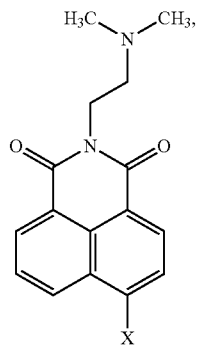

including salts, esters, and prodrugs thereof; and including both R and S enantiomeric forms and racemic mixtures thereof; wherein X is present or absent, and if present is

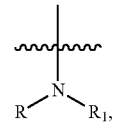

wherein R is H, ethyl, or R1, and wherein R1 is H,

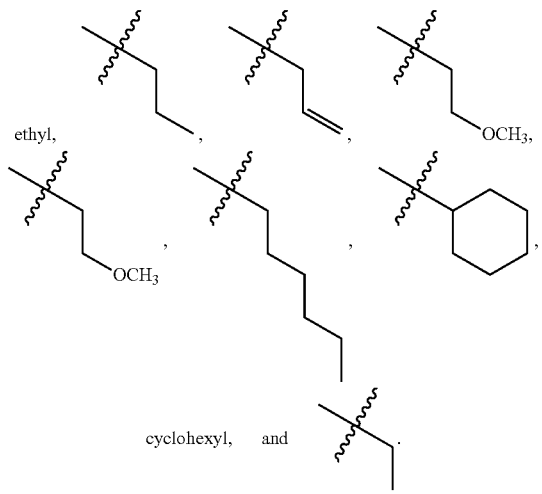

The present invention is not limited to a particular type of compound. In some embodiments, the compound is one of the following compounds:

(A1)

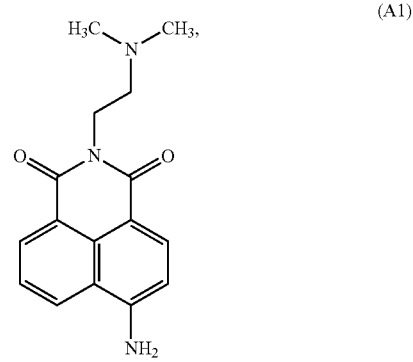

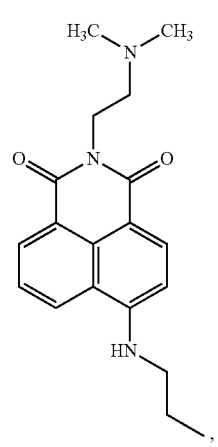 (A2)
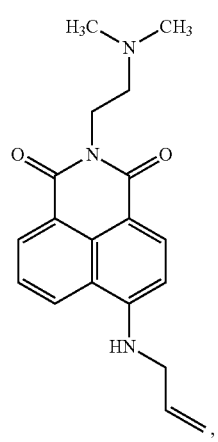 (A3)
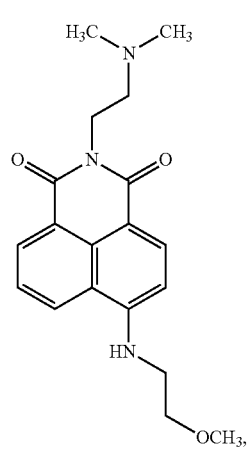 (A4)
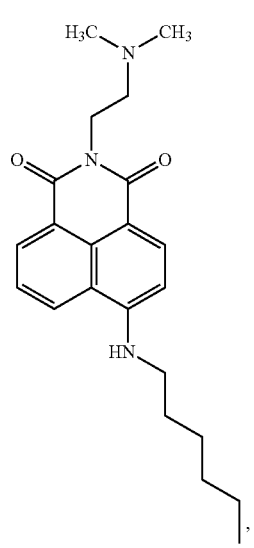 (A5)
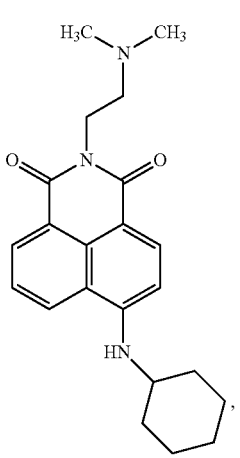 (A6)
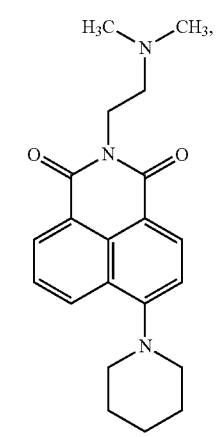 (A7)

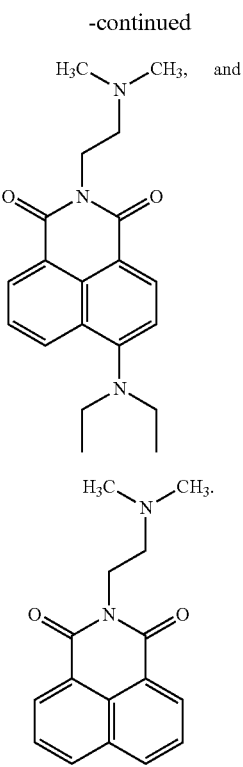

(A8)

(A9)

In certain embodiments, the present invention provides pharmaceutical preparations comprising one or more of the compounds and a pharmaceutically acceptable carrier. In some embodiments, the present invention provides methods for treating a hyperproliferative disorder comprising administering an effective amount of the pharmaceutical preparation to a subject in need thereof. The present invention is not limited to a particular type of hyperproliferative disorder. In some embodiments, the hyperproliferative disorder is a cancer (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, bladder cancer, leukemia cancer, prostate cancer, renal cancer, uterine cancer, ovarian cancer, breast cancer, colon cancer, cervical cancer, and lung cancer). In some embodiments, the methods comprise co-administering to the subject an anti-cancer agent (e.g., Acivicin; Aclarubicin; Acodazole Hydrochloride; Acronine; Adozelesin; Adriamycin; Aldesleukin; Alitretinoin; Allopurinol Sodium; Altretamine; Ambomycin; Ametantrone Acetate; Aminoglutethimide; Amsacrine; Anastrozole; Annonaceous Acetogenins; Anthramycin; Asimicin; Asparaginase; Asperlin; Azacitidine; Azetepa; Azotomycin; Batimastat; Benzodepa; Bexarotene; Bicalutamide; Bisantrene Hydrochloride; Bisnafide Dimesylate; Bizelesin; Bleomycin Sulfate; Brequinar Sodium; Bropirimine; Bullatacin; Busulfan; Cabergoline; Cactinomycin; Calusterone; Caracemide; Carbetimer; Carboplatin; Carmustine; Carubicin Hydrochloride; Carzelesin; Cedefingol; Celecoxib; Chlorambucil; Cirolemycin; Cisplatin; Cladribine; Crisnatol Mesylate; Cyclophosphamide; Cytarabine; Dacarbazine; DACA (N-[2-(Dimethyl-amino)ethyl]acridine-4-carboxamide); Dactinomycin; Daunorubicin Hydrochloride; Daunomycin; Decitabine; Denileukin Diftitox; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Fluorocitabine; Fosquidone; Fostriecin Sodium; FK-317; FK-973; FR-66979; FR-900482; Gemcitabine; Geimcitabine Hydrochloride; Gemtuzumab Ozogamicin; Gold Au 198; Goserelin Acetate; Guanacone; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Methoxsalen; Metoprine; Meturedepa; Mitindomide; Mitocarcin; Mitocromin; Mitogillin; Mitomalcin; Mitomycin; Mytomycin C; Mitosper; Mitotane; Mitoxantrone Hydrochloride; Mycophenolic Acid; Nocodazole; Nogalamycin; Oprelvekin; Ormaplatin; Oxisuran; Paclitaxel; Pamidronate Disodium; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rituximab; Rogletimide; Rolliniastatin; Safingol; Safingol Hydrochloride; Samarium/Lexidronam; Semustine; Simtrazene; Sparfosate Sodium; Sparsomycin; Spirogermanium Hydrochloride; Spiromustine; Spiroplatin; Squamocin; Squamotacin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trastuzumab; Trestolone Acetate; Triciribine Phosphate; Trimetrexate; Trimetrexate Glucuronate; Triptorelin; Tubulozole Hydrochloride; Uracil Mustard; Uredepa; Valrubicin; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid; 2-chloro-2'- arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlorethamine); cyclophosphamide; melphalan; chlorambucil; ifosfamide; busulfan; N-methyl-N-nitrosourea (MNU); N,N'-Bis(2-chloroethyl)-N-nitrosourea (BCNU); N-(2-chloroethyl)-N'-cyclohex-yl-N-nitrosourea (CCNU); N-(2-chloroethyl)-N'-(trans-4-methylcyclohexyl-N-nitrosourea (MeCCNU); N-(2-chloroethyl)-N'-(diethyl) ethylphosphonate-N-nit-rosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis (platinum); tomudex; azacitidine; cytarabine; gemcitabine; 6-Mercaptopurine; 6-Thioguanine; Hypoxanthine; teniposide; 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl) retinamide; 13-cis retinoic acid; 3-Methyl TTNEB; 9-cis retinoic acid; fludarabine (2-F-ara-AMP); 2-chlorodeoxyadenosine (2-Cda), Antiproliferative agents, Piritrexim Isothionate, Antiprostatic hypertrophy agents, Sitogluside, Benign prostatic hyperplasia therapy agents, Tamsulosin Hydrochloride, Prostate growth inhibitor agents, Pentomone, and Radioactive agents, Fibrinogen 1 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m Sulfur Colloid; Technetium Tc 99m Teboroxime; Technetium Tc 99m Tetrofosmin; Technetium Tc 99m Tiatide; Thyroxine I 125; Thyroxine I 131; Tolpovidone I 131; Triolein I 125; and Triolein I 131).

Figure 1:
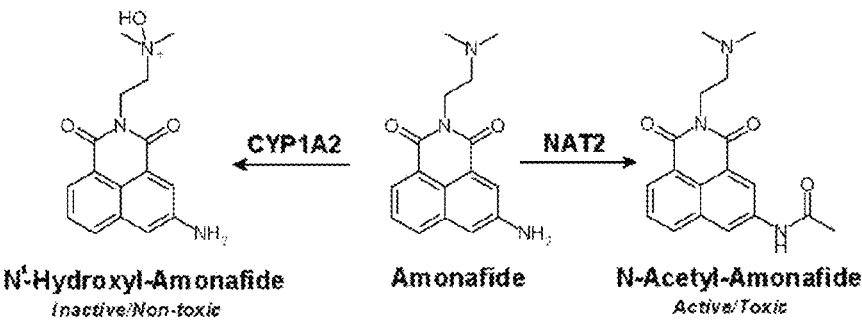
FIG. 1 shows synthesis of amonafide derivatives. (A) CYP1A2 is responsible for the inactivation of amonafide and NAT2 is responsible for the production of the toxic N-acetyl species. (B) Synthesis scheme for A1-A9. (C) In vitro NAT2 acetylation assay demonstrates 6-position amino derivatives cannot be acetylated. Recombinant human NAT2 enzyme and mass spectrometry were used to determine if the novel derivatives can be metabolized by this enzyme. Amonafide is a positive control, A1 is an unknown as it has a 6-position free aryl amine, and A2 is a representative negative control as it does not have a free aryl amine and therefore cannot be acetylated by NAT2, which requires a substrate free amine for activity.
Figure 1:
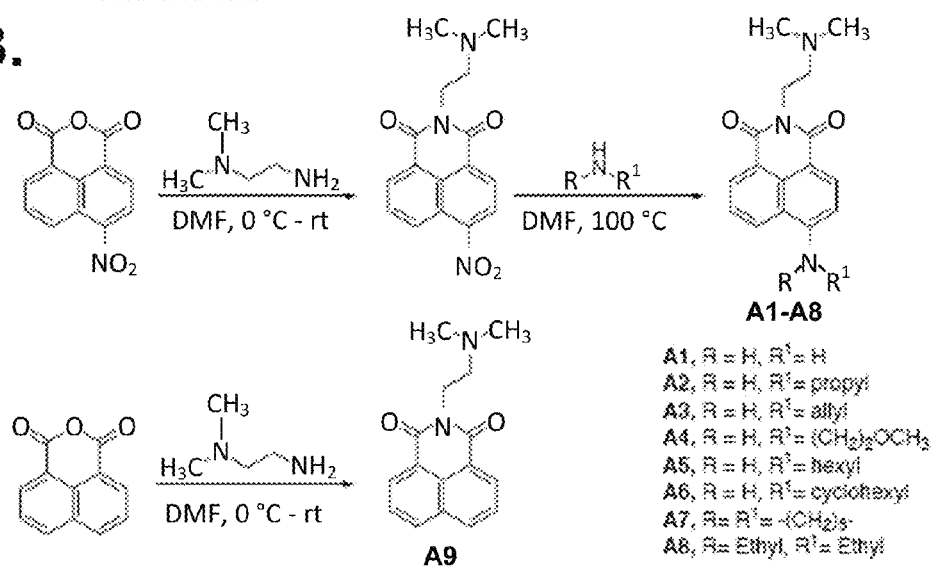
Figure 1:
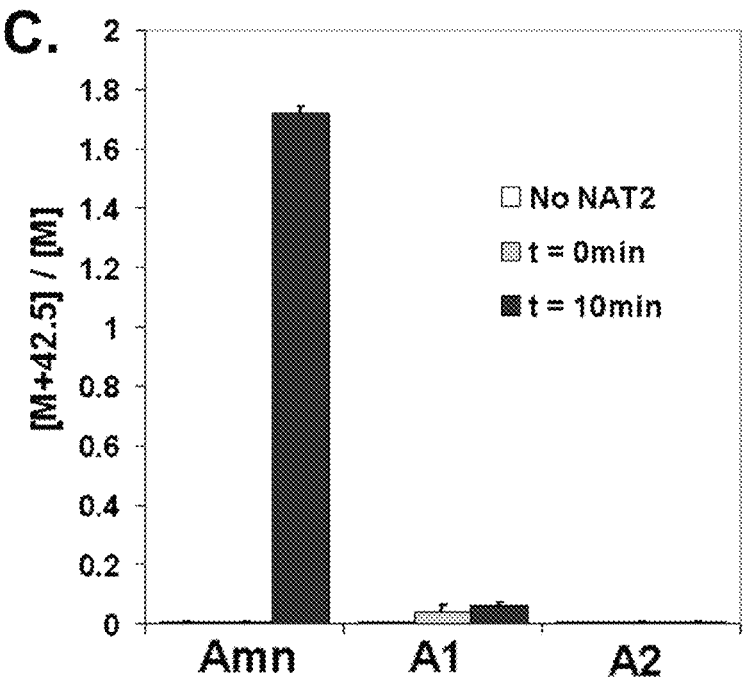

PTB localizes to the nucleoplasm (excluding nucleoli) and is highly concentrated in the PNC if present. Exemplary PNCs are marked with arrow heads. Scale bar=10 μm. Bottom panel: Quantification of PNC prevalence reduction in HeLa cells treated with the [$IC_{50\%}$] (gray bar) or the [$IC_{99\%}$] (black bar) of each compound (error bars=+SD). Amonafide, A1, and A4 are the only compounds that can significantly reduce PNC prevalence at their [$IC_{50\%}$], while all the derivatives except A5 can significantly reduce PNC prevalence at their [$IC_{99\%}$].

DEFINITIONS

To facilitate an understanding of the present invention, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject is suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass) but for whom a confirmatory test (e.g., biopsy and/or histology) has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. A "preliminary diagnosis" is one based only on visual (e.g., CT scan or the presence of a lump) and antigen tests. As used herein, the term "subject at risk for cancer" refers to a subject with one or more risk factors for developing a specific cancer. Risk factors include, but are not limited to, gender, age, genetic predisposition, environmental expose, and previous incidents of cancer, preexisting non-cancer diseases, and lifestyle.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

As used herein, the term "effective amount" refers to the amount of a composition (e.g., comprising a compound of the present invention) sufficient to effect beneficial or desired results. An effective amount can be administered in one or more administrations, applications or dosages and is not intended to be limited to a particular formulation or administration route.

As used herein, the term "administration" refers to the act of giving a drug, prodrug, or other agent, or therapeutic treatment (e.g., compositions of the present invention) to a subject (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like.

As used herein, the term "co-administration" refers to the administration of at least two agent(s) (e.g., a compound of the present invention and an anti-cancer agent) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

As used herein, the term "toxic" refers to any detrimental or harmful effects on a subject, a cell, or a tissue as compared to the same cell or tissue prior to the administration of the toxicant.

As used herein, the term "pharmaceutical composition" refers to the combination of an active agent (e.g., a compound of the present invention) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "topically" refers to application of the compositions of the present invention to the surface of the skin and mucosal cells and tissues (e.g., alveolar, buccal, lingual, masticatory, or nasal mucosa, and other tissues and cells that line hollow organs or body cavities).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. (1975), incorporated herein by reference in its entirety).

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the terms "6-position amino derivative" refer to 6-amino-2-[2-(dimethylamino)ethyl]1H-Benz[de]isoquinoline-1,3(2H)-diones.

As used herein, the terms "drug" and "chemotherapeutic agent" refer to pharmacologically active molecules that are used to diagnose, treat, or prevent diseases or pathological conditions in a physiological system (e.g., a subject, or in vivo, in vitro, or ex vivo cells, tissues, and organs). Drugs act by altering the physiology of a living organism, tissue, cell, or in vitro system to which the drug has been administered. It is intended that the terms "drug" and "chemotherapeutic agent" encompass anti-hyperproliferative and antineoplastic compounds as well as other biologically therapeutic compounds.

The terms "analog" and "derivative" of a compound, as used herein, refers to a chemically modified compound wherein the chemical modification takes place either at a functional group of the compound, aromatic ring, or carbon backbone. Such derivatives include esters of alcohol-containing compounds, esters of carboxy-containing compounds, amides of amine-containing compounds, amides of carboxy-containing compounds, imines of amino-containing compounds, acetals of aldehyde-containing compounds, ketals of carbonyl-containing compounds, and the like. The term "6-position amino derivative" specifically refers to 6-amino-2-[2-(dimethylamino)ethyl]1H-Benz[de]isoquinoline-1,3(2H)-diones.

A "hyperproliferative disease," as used herein refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A "metastatic" cell or tissue means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell. Metaplasia can occur in epithelial or connective tissue cells. A typical metaplasia involves a somewhat disorderly metaplastic epithelium.

As used herein, the term "neoplastic disease" refers to any abnormal growth of cells or tissues being either benign (non-cancerous) or malignant (cancerous).

As used herein the term, "in vitro" refers to an artificial environment and to processes or reactions that occur within an artificial environment. In vitro environments can consist of, but are not limited to, test tubes. The term "in vivo" refers to the natural environment (e.g. cell culture) and to processes or reactions that occur within a natural environment.

As used herein, the term "cell culture" refers to any culture of cells. Included within this term are continuous cell lines (e.g., with an immortal phenotype), primary cell cultures, finite cell lines (e.g., non-transformed cells), and any other cell population maintained in culture, including oocytes and embryos.

DETAILED DESCRIPTION OF THE INVENTION

Amonafide is a DNA intercalator and topoisomerase II (topo II) inhibitor [1-3] that has shown good activity in several clinical trials [4-6]. The malate salt of amonafide and the dihyrdochloride salt is currently under clinical development for the treatment of acute myelocytic leukemia [7] and the dihyrdochloride salt is under clinical development for the treatment of refractory prostate carcinoma [8]. Amonafide is converted to two main metabolites in humans, which are an inactive/non-toxic N'-hydroxylated metabolite and an active/toxic N-acetyl metabolite [9-13] (FIG. 1A). The latter is produced by N-acetyl transferase 2 (NAT2) [12], which is a polymorphic enzyme causing differential acetylation activity among individuals [13]. N-acetyl amonafide has been suggested to compete for metabolic inactivation via CYP1A2 (FIG. 1A) with the parent drug causing increased plasma levels of active drug, hence causing toxicities [9]. Patients that are phenotyped as fast acetylators produce higher levels of the toxic N-acetylated metabolite causing increased drug related toxicities compared to slow acetylators [14]. The extent of this differential acetylation causes some slow acetylators to be severely under dosed and some fast acetylators to experience grade 4 toxicities at a fixed dose [9]. This problem has forced physicians to determine patient's acetylator status based on caffeine (a substrate for NAT2) acetylation rate [9, 15] or by genotyping [8] in order to optimize the dose of amonafide for each group. These phenotyping/genotyping assays delay treatment and add cost to the treatment regimen. In addition, once phenotyped or genotyped, fast acetylators receive a lower dose of amonafide [15], which may decrease the efficacy of amonafide treatment for this group of patients.

A derivative of amonafide that cannot be acetylated, but retains biological activity, may allow consistent treatment regimens for patients independent of acetylator phenotype. This hypothesis has been addressed in previous studies with the creation of the amonafide derivatives, azonafide [16] and mitonafide [17]. Azonafide contains an anthracene ring instead of the naphthalene ring of amonafide, and has no free aryl amine. Mitonafide has a nitro group in the 5-position, instead of the free amine of amonafide. Both of these compounds avoid NAT2 based metabolism due a lack of an aryl amine and both are effectively cytotoxic to cultured cancer cells [17-18]. Also, very potent bis-napthalamide derivatives, including elinafide, that lack an aryl amine have been synthesized [19-20]; however, each of the derivatives mentioned is chemically much different from amonafide, which most likely affects the target, cellular uptake, and/or bioavailability of the drugs. Therefore, there is still a need for an amonafide derivative that is not able to be metabolized by NAT2, but is chemically similar to amonafide and retains the potency, selectivity, and biological activity of amonafide.

Experiments conducted during the course of development of embodiments for the present invention investigated derivatives of amonafide that cannot be acetylated by NAT2, while maintaining biological activities similar to (e.g., better than) amonafide. Such derivatives were synthesized by moving the free aryl amine from the 5- to the 6-position, by adding functional groups to the 6-position amine, and/or by completely removing the aryl amine. Nine derivatives were synthesized and the biological activities of each were directly compared with amonafide and other pertinent controls using purified systems and in vitro assays. In particular, eight derivatives have aryl amines at the 6-position (vs. 5-position of amonafide) and one derivative completely lacks the aryl amine. The derivative with a free amine in the 6-position and one with a substituted amine in the 6-position are not acetylated while amonafide is extensively acetylated as determined by an NAT2 assay. The biological activities of these compounds were evaluated to determine if they behaved similarly to amonafide in purified systems and in vitro. It was found that three compounds had similar cancer cell-selective growth inhibition to amonafide, while also retaining similar subcellular localization, DNA intercalation and topoisomerase II inhibition activities. In addition, these compounds were able to eliminate a marker of metastatic potential, the perinucleolar compartment. Thus, these three compounds (named numonafides) allow for better patient management than those treated with amonafide and hence should be developed further as potential clinical replacements for amonafide or as novel anti-cancer drugs.

Exemplary compositions and methods of the present invention are described in more detail in the following sections: I. Exemplary Compounds; II. Pharmaceutical compositions, formulations, and exemplary administration routes and dosing considerations; and III. Therapeutic Applications.

The practice of the present invention employs, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "Molecular cloning: a laboratory manual" Second Edition (Sambrook et al., 1989); "Oligonucleotide synthesis" (M. J. Gait, ed., 1984); "Animal cell culture" (R. I. Freshney, ed., 1987); the series "Methods in enzymology" (Academic Press, Inc.); "Handbook of experimental immunology" (D. M. Weir & C. C. Blackwell, eds.); "Gene transfer vectors for mammalian cells" (J. M. Miller & M. P. Calos, eds., 1987); "Current protocols in molecular biology" (F. M. Ausubel et al., eds., 1987, and periodic updates); "PCR: the polymerase chain reaction" (Mullis et al., eds., 1994); and "Current protocols in immunology" (J. E. Coligan et al., eds., 1991), each of which is herein incorporated by reference in its entirety.

I. Exemplary Compounds

Exemplary compounds of the present invention are provided below. In certain embodiments, the present invention provides compounds described by the following formulas:

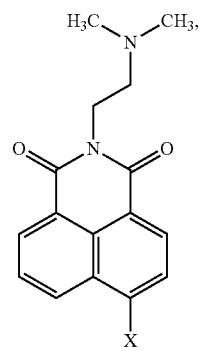

including salts, esters, and prodrugs thereof; and including both R and S enantiomeric forms and racemic mixtures thereof; wherein X is present or absent, and if present is

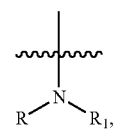

wherein R is H, ethyl, or R1, and wherein R1 is H,

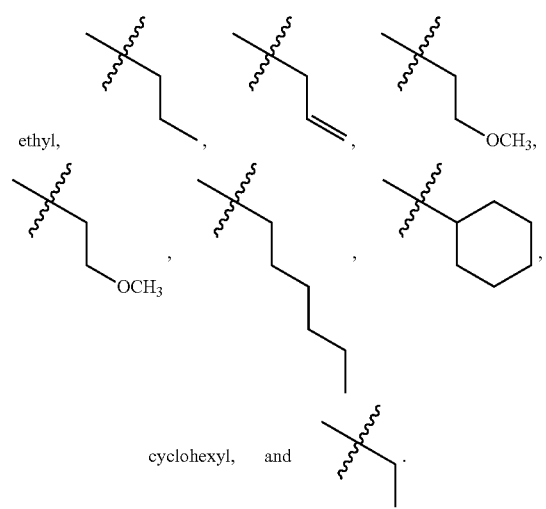

cyclohexyl, and

In certain embodiments, the present invention provides the following compounds:

(A1)

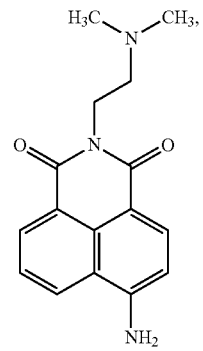

-continued
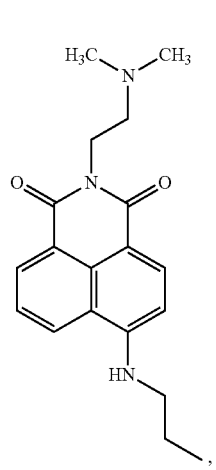 (A2)
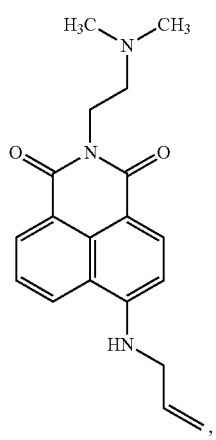 (A3)
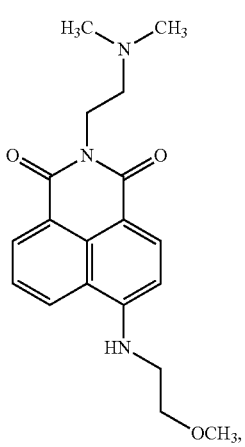 (A4)
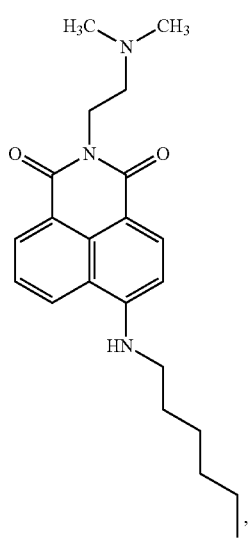 (A5)
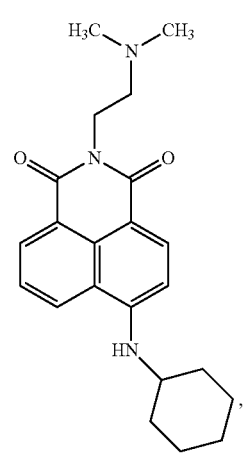 (A6)
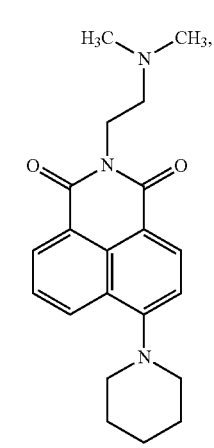 (A7)

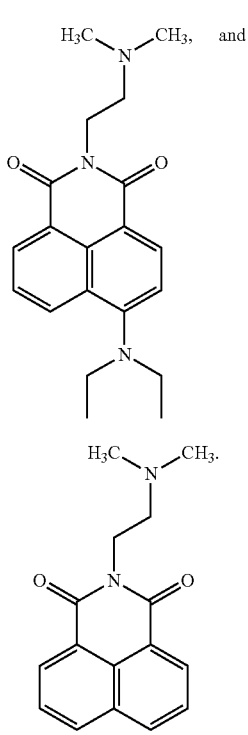

(A8)

(A9)

II. Pharmaceutical Compositions, Formulations, and Exemplary Administration Routes and Dosing Considerations Exemplary embodiments of various contemplated medicaments and pharmaceutical compositions are provided below.

A. Preparing Medicaments

It is contemplated that the compounds of the present invention are useful in the preparation of medicaments to treat a variety of conditions associated with cancer and/or hyperproliferation.

In addition, it is contemplated that the compounds are also useful for preparing medicaments for treating other disorders wherein the effectiveness of the compounds are known or predicted. Such disorders include, but are not limited to, neurological (e.g., epilepsy) or neuromuscular disorders. The methods and techniques for preparing medicaments of a compound of the present invention are well-known in the art. Exemplary pharmaceutical formulations and routes of delivery are described below.

One of skill in the art will appreciate that any one or more of the compounds described herein, including the many specific embodiments, are prepared by applying standard pharmaceutical manufacturing procedures. Such medicaments can be delivered to the subject by using delivery methods that are well-known in the pharmaceutical arts.

B. Exemplary Pharmaceutical Compositions and Formulation

In some embodiments of the present invention, the compositions are administered alone, while in some other embodiments, the compositions are preferably present in a pharmaceutical formulation comprising at least one active ingredient/agent, as defined above, together with a solid support or alternatively, together with one or more pharmaceutically acceptable carriers and optionally other therapeutic agents. Each carrier must be "acceptable" in the sense that it is compatible with the other ingredients of the formulation and not injurious to the subject.

Contemplated formulations include those suitable oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In other embodiments, the active ingredient is presented as a bolus, electuary, or paste, etc.

In some embodiments, tablets comprise at least one active ingredient and optionally one or more accessory agents/carriers are made by compressing or molding the respective agents. In some embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose)surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention are optionally formulated as ointments, creams, suspensions, lotions, powders, solutions, pastes, gels, sprays, aerosols or oils. In alternatively embodiments, topical formulations comprise patches or dressings such as a bandage or adhesive plasters impregnated with active ingredient(s), and optionally one or more excipients or diluents. In some embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of this invention are constituted from known ingredients in an known manner. This phase typically comprises an lone emulsifier (otherwise known as an emulgent), it is also desirable in some embodiments for this phase to further comprises a mixture of at least one emulsifier with a fat or an oil or with both a fat and an oil.

Preferably, a hydrophilic emulsifier is included together with a lipophilic emulsifier so as to act as a stabilizer. It some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with suitable base comprising, for example, cocoa butter or a salicylate.

Formulations suitable for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, an include aqueous or oily solutions of the agents.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, and stabilizers, etc.

In some embodiments, the compounds of the present invention are provided in unsolvated form or are in non-aqueous solutions (e.g., ethanol). The compounds may be generated to allow such formulations through the production of specific crystalline polymorphs compatible with the formulations.

In certain embodiments, the present invention provides instructions for administering said compound to a subject. In certain embodiments, the present invention provides instructions for using the compositions contained in a kit for the treatment of conditions characterized by the conditions associated with cancer and/or hyperproliferation (e.g., providing dosing, route of administration, decision trees for treating physicians for correlating patient-specific characteristics with therapeutic courses of action). In certain embodiments, the present invention provides instructions for using the compositions contained in the kit to treat cancer and/or hyperproliferative disorders (e.g., tumors, B cell lymphomas, T cell lymphomas, etc.).

C. Exemplary Administration Routes and Dosing Considerations

Various delivery systems are known and can be used to administer therapeutic agents (e.g., exemplary compounds as described in Section I above) of the present invention, e.g., encapsulation in liposomes, microparticles, microcapsules, receptor-mediated endocytosis, and the like. Methods of delivery include, but are not limited to, intra-arterial, intra-muscular, intravenous, intranasal, and oral routes. In specific embodiments, it may be desirable to administer the pharmaceutical compositions of the invention locally to the area in need of treatment; this may be achieved by, for example, and not by way of limitation, local infusion during surgery, injection, or by means of a catheter.

It is contemplated that the agents identified can be administered to subjects or individuals susceptible to or at risk of developing pathological growth of target cells and correlated conditions. When the agent is administered to a subject such as a mouse, a rat or a human patient, the agent can be added to a pharmaceutically acceptable carrier and systemically or topically administered to the subject. To determine patients that can be beneficially treated, a tissue sample is removed from the patient and the cells are assayed for sensitivity to the agent.

Therapeutic amounts are empirically determined and vary with the pathology being treated, the subject being treated and the efficacy and toxicity of the agent.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient.

Desirable blood levels of the agent may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

D. Exemplary Co-Administration Routes and Dosing Considerations

The present invention also includes methods involving co-administration of the compounds described herein with one or more additional active agents. Indeed, it is a further aspect of this invention to provide methods for enhancing prior art therapies and/or pharmaceutical compositions by co-administering a compound of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered chemical agents, biological agents or radiation may each be administered using different modes or different formulations.

The agent or agents to be co-administered depends on the type of condition being treated. For example, when the condition being treated is cancer, the additional agent can be a chemotherapeutic agent or radiation. The additional agents to be co-administered and can be any of the well-known agents in the art, including, but not limited to, those that are currently in clinical use. The determination of appropriate type and dosage of radiation treatment is also within the skill in the art or can be determined with relative ease.

The present invention is not limited by type of anti-cancer agent co-administered. Indeed, a variety of anti-cancer agents are contemplated to be useful in the present invention including, but not limited to, Acivicin; Aclarubicin; Acodazole Hydrochloride; Acronine; Adozelesin; Adriamycin; Aldesleukin; Alitretinoin; Allopurinol Sodium; Altretamine; Ambomycin; Ametantrone Acetate; Aminoglutethimide; Amsacrine; Anastrozole; Annonaceous Acetogenins; Anthramycin; Asimicin; Asparaginase; Asperlin; Azacitidine; Azetepa; Azotomycin; Batimastat; Benzodepa; Bexarotene; Bicalutamide; Bisantrene Hydrochloride; Bisnafide Dimesylate; Bizelesin; Bleomycin Sulfate; Brequinar Sodium; Bropirimine; Bullatacin; Busulfan; Cabergoline; Cactinomycin; Calusterone; Caracemide; Carbetimer; Carboplatin; Carmustine; Carubicin Hydrochloride; Carzelesin; Cedefingol; Celecoxib; Chlorambucil; Cirolemycin; Cisplatin; Cladribine; Crisnatol Mesylate; Cyclophosphamide; Cytarabine; Dacarbazine; DACA (N-[2-(Dimethyl-amino)ethyl] acridine-4-carboxamide); Dactinomycin; Daunorubicin Hydrochloride; Daunomycin; Decitabine; Denileukin Diftitox; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Fluorocitabine; Fosquidone; Fostriecin Sodium; FK-317; FK-973; FR-66979; FR-900482; Gemcitabine; Geimcitabine Hydrochloride; Gemtuzumab Ozogamicin; Gold Au 198; Goserelin Acetate; Guanacone; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Methoxsalen; Metoprine; Meturedepa; Mitindomide; Mitocarcin; Mitocromin; Mitogillin; Mitomalcin; Mitomycin; Mytomycin C; Mitosper; Mitotane; Mitoxantrone Hydrochloride; Mycophenolic Acid; Nocodazole; Nogalamycin; Oprelvekin; Ormaplatin; Oxisuran; Paclitaxel; Pamidronate Disodium; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rituximab; Rogletimide; Rolliniastatin; Safingol; Safingol Hydrochloride; Samarium/Lexidronam; Semustine; Simtrazene; Sparfosate Sodium; Sparsomycin; Spirogermanium Hydrochloride; Spiromustine; Spiroplatin; Squamocin; Squamotacin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trastuzumab; Trestolone Acetate; Triciribine Phosphate; Trimetrexate; Trimetrexate Glucuronate; Triptorelin; Tubulozole Hydrochloride; Uracil Mustard; Uredepa; Valrubicin; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid; 2-chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlorethamine); cyclophosphamide; melphalan; chlorambucil; ifosfamide; busulfan; N-methyl-N-nitrosourea (MNU); N,N'-Bis(2-chloroethyl)-N-nitrosourea (BCNU); N-(2-chloroethyl)-N'-cyclohex-yl-N-nitrosourea (CCNU); N-(2-chloroethyl)-N'-(trans-4-methylcyclohexyl-N-nitrosourea (MeCCNU); N-(2-chloroethyl)-N'-(diethyl) ethylphosphonate-N-nit-rosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis (platinum); tomudex; azacitidine; cytarabine; gemcitabine; 6-Mercaptopurine; 6-Thioguanine; Hypoxanthine; teniposide; 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl) retinamide; 13-cis retinoic acid; 3-Methyl TTNEB; 9-cis retinoic acid; fludarabine (2-F-ara-AMP); and 2-chlorodeoxyadenosine (2-Cda).

Other anti-cancer agents include: Antiproliferative agents (e.g., Piritrexim Isothionate), Antiprostatic hypertrophy agent (e.g., Sitogluside), Benign prostatic hyperplasia therapy agents (e.g., Tamsulosin Hydrochloride), Prostate growth inhibitor agents (e.g., Pentomone), and Radioactive agents: Fibrinogen 1 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m Sulfur Colloid; Technetium Tc 99m Teboroxime; Technetium Tc 99m Tetrofosmin; Technetium Tc 99m Tiatide; Thyroxine I 125; Thyroxine I 131; Tolpovidone I 131; Triolein I 125; Triolein I 131.

Another category of anti-cancer agents is anti-cancer Supplementary Potentiating Agents, including: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{++}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL.

Still other anticancer agents are those selected from the group consisting of: annonaceous acetogenins; asimicin; rolliniastatin; guanacone, squamocin, bullatacin; squamotacin; taxanes; paclitaxel; gemcitabine; methotrexate FR-900482; FK-973; FR-66979; FK-317; 5-FU; FUDR; FdUMP; Hydroxyurea; Docetaxel; discodermolide; epothilones; vincristine; vinblastine; vinorelbine; meta-pac; irinotecan; SN-38; 10-OH campto; topotecan; etoposide; adriamycin; flavopiridol; Cis-Pt; carbo-Pt; bleomycin; mitomycin C; mithramycin; capecitabine; cytarabine; 2-C1-2' deoxyadenosine; Fludarabine-$PO_4$; mitoxantrone; mitozolomide; Pentostatin; and Tomudex.

One particularly preferred class of anticancer agents are taxanes (e.g., paclitaxel and docetaxel). Another important category of anticancer agent is annonaceous acetogenin.

Other cancer therapies include hormonal manipulation. In some embodiments, the anti-cancer agent is tamoxifen or the aromatase inhibitor arimidex (i.e., anastrozole).

III. Therapeutic Application

In certain embodiments, the present invention provides methods (e.g., therapeutic applications) for regulating treating conditions associated with cancer and/or hyperproliferation comprising: a) providing: i. a subject (e.g., a human subject diagnosed with cancer) diagnosed with cancer; and ii. a composition (e.g., exemplary compounds as described in Section III above); and b) exposing the subject to the composition under conditions such that the exposure results in cancer cell death. The present invention is not limited to a particular therapeutic application. Non-limiting examples of therapeutic applications for the present invention are described in the following subsections. The present invention is not limited to treating particular types of cancer. Examples of cancer include, but are not limited to, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, bladder cancer, leukemia cancer, prostate cancer, renal cancer, uterine cancer, ovarian cancer, breast cancer, colon cancer, cervical cancer, and lung cancer. In some embodiments, the compositions of the present invention are co-administered with one or more additional treatment agents (e.g., anti-cancer agents described in Section II).

EXPERIMENTAL

The following examples are provided in order to demonstrate and further illustrate certain preferred embodiments and aspects of the present invention and are not to be construed as limiting the scope thereof.

Methods

Chemical Synthesis

A total of eight amonafide derivatives with amines in the 6-position were synthesized (A1 to A8) as well as a derivative completely lacking an aryl amine (A9). The synthesis scheme is shown in FIG. 1B and the synthesis details are listed below. A1 and A9 have been synthesized previously [21, 17]. Amonafide was obtained from the National Cancer Institute's Developmental Therapeutics Program (Bethesda, Md.). All compounds were stored at 10 mM in DMSO at −20° C.

Analysis of synthetic products: Proton nuclear magnetic resonances ($^1$H NMR) were recorded in deuterated solvents on a Gemini 300 (300 MHz) or iNOVA 500 (500 MHz) spectrometer. Chemical shifts are reported in parts per million (ppm, δ) relative to tetramethylsilane (δ0.00). If tetramethylsilane was not present, the residual protio solvent is referenced (CDCl$_3$, δ 7.27; dimethylsulfoxide-d$_6$ (DMSO-d$_6$), δ 2.50). $^1$H NMR splitting patterns are designated as singlet (s), doublet (d), triplet (t), or quartet (q). Splitting patterns that could not be interpreted or easily visualized were designated as multiplet (m) or broad (br). In some cases, the signals from exchangeable protons were not able to be identified. Coupling constants are reported in Hertz (Hz). Mass spectra were obtained using an API 3000 LC/MS/MS system, a Micromass Quattro II Triple Quadrupole HPLC/MS/MS Mass Spectrometer, or a Waters LCT Premier time-of-flight (TOF) mass spectrometer. Analytical thin layer chromatography (TLC) was carried out on Sorbent Technologies TLC plates precoated with silica gel (250 μm layer thickness). Flash column chromatography was performed on EM Science silica gel 60 (230-400 mesh). All commercially available reagents and solvents were purchased from Aldrich (St. Louis, Mo.) and used without further purification except for dimethylformamide (DMF), which was purified by passage through a bed of activated alumina.

Synthesis of 6-nitro-imide precursor (6-nitro-2-[2-(dimethylamino)ethyl]-1H-benz[de]isoquinoline-1,3(2H)-dione): 6-nitro-naphthylic anhydride (1.00 g, 4.11 mmol) was dissolved in DMF (40 mL) and the solution was cooled to 0° C. and N,N-dimethylethylene diamine (0.45 mL, 4.11 mmol) was added dropwise. The solution was allowed to warm to room temperature and stirred for 24 hours. The solvent was removed under vacuum and purified by flash column chromatography to yield 1.24 g (96%) 4-nitro-N-(dimethylaminoethyl)naphthylic imide as a light brown solid. $^1$H NMR (500 MHz, CDCl$_3$) δ 8.84 (d, J=8.0 Hz, 1H, naphthylic-H) 8.40 (d, J=7.5 Hz, 1H, naphthylic-H) 8.69 (d, J=8.0 Hz, 1H, naphthylic-H) 8.40 (d, J=8.0 Hz, 1H, naphthylic-H) 7.99 (t, J=8.0 Hz, 1H, naphthylic-H) 4.34 (t, J=7.0 Hz, 2H, ethylene-CH$_2$) 2.67 (t, J=7.0 Hz, 2H, ethylene-CH$_2$) 2.34 (s, 6H, N(CH$_3$)$_2$). Calculated mass for [M+H]$^+$=314.11; observed=314.2.

Synthesis of A1 (6-amino-2-[2-(dimethylamino)ethyl]-1H-benz[de]isoquinoline-1,3(2H)-dione): Nitro-N-(dimethylaminoethyl)naphthalic imide (200 mg, 0.64 mmol) was dissolved in 95% ethanol and slowly added to a Parr flask containing 10% Pd/C. The mixture was placed on a Parr apparatus under 40 psi H$_2$ pressure for 12 hours. The mixture was filtered through Celite and the solvent was removed under vacuum. 6-nitro-N-(dimethylaminoethyl)naphthalic imide was reduced via hydrogenolysis to yield 185 mg (99%) A1 as a bright orange solid. $^1$H NMR (300 MHz, CDCl$_3$) δ 8.57 (d, J=7.0 Hz, 1H, naphthylic-H) 8.34 (d, J=8.0 Hz, 1H, naphthylic-H) 8.05 (d, J=8.5 Hz, 1H, naphthylic-H) 7.62 (t, 1H, naphthylic-H) 6.79 (d, J=8.0 Hz, 1H, naphthylic-H) 5.04 (br s, 2H, amino-H) 4.32 (t, J=6.5 Hz, 2H, ethylene-CH$_2$) 2.68 (t, J=6.5 Hz, 2H, ethylene-CH$_2$) 2.38 (s, 6H, N(CH$_3$)$_2$). Calculated mass for [M+H]$^+$=284.14; observed=284.14.

Synthesis of A2 (6-propylamino-2-[2-(dimethylamino)ethyl]-1H-benz[de]isoquinoline-1,3(2H)-dione): 6-nitro-imide precursor (1.00 g, 3.19 mmol) was added to a high-pressure vessel and the solid was suspended in DMF (2 mL). Excess propylamine (1.0 mL) was added turning the suspension dark brown. The vessel was tightly sealed and heated to 100° C. for one hour. The solution was cooled to room temperature and the solvents were removed under vacuum. The dark brown residue was purified by flash column chromatography (5% MeOH/CH$_2$Cl$_2$) to yield 548 mg (53%) of A2 as a bright orange solid. This procedure was used for A3-A8 as well. $^1$H NMR (500 MHz, CDCl$_3$) δ 8.58 (d, J=7.0 Hz, 1H, naphthylic-H) 8.47 (d, J=8.5 Hz, 1H, naphthylic-H) 8.08 (d, J=8.5 Hz, 1H, naphthylic-H) 7.62 (t, J=8.0 Hz, 1H, naphthylic-H) 6.73 (d, J=8.5 Hz, 1H, naphthylic-H) 5.24 (br s, 1H, amino-H) 4.33 (t, J=7.0 Hz, 2H, ethylene-CH$_2$) 3.39 (m, 2H, NHCH$_2$CH$_2$CH$_3$) 2.69 (t, J=7.0 Hz, 2H, ethylene-CH$_2$) 2.40 (s, 6H, N(CH$_3$)$_2$) 1.85 (m, 2H, NHCH$_2$CH$_2$CH$_3$) 1.12 (t, J=7.0 Hz, 3H, NHCH$_2$CH$_2$CH$_3$). Calculated mass for [M+H]$^+$=326.19; observed=326.1.

Synthesis of A3 (6-allylamino-2-[2-(dimethylamino)ethyl]-1H-benz[de]isoquinoline-1,3(2H)-dione): 6-nitro-imide precursor (200 mg, 0.64 mmol) and excess allylamine (0.5 mL) in DMF (1 mL), were reacted to yield 89.4 mg (43%) of A3 as a bright orange solid. $^1$H NMR (300 MHz, CDCl$_3$) δ 8.59 (dd, J=7.2 Hz, 1H, naphthylic-H) 8.46 (d, J=8.4 Hz, 1H, naphthylic-H) 8.10 (dd, J=7.8 Hz, 1H, naphthylic-H) 7.63 (dd, J=7.8 Hz, 1H, naphthylic-H) 6.73 (d, J=8.4 Hz, 1H, naphthylic-H) 6.10-6.00 (ddt, 1H, CH$_2$CHCH$_2$) 5.45-5.30 (m, 2H, terminal alkene-H) 4.32 (t, J=7.2 Hz, 2H, ethylene-CH$_2$) 3.39 (m, 2H, allylic-H) 2.65 (t, J=7.2 Hz, 2H, ethylene-CH$_2$) 2.40 (s, 6H, N(CH$_3$)$_2$). Calculated mass for [M+H]$^+$=324.40; observed=324.5.

Synthesis of A4 (6-methoxyethylamino-2-[2-(dimethylamino)ethyl]-1H-benz[de]isoquinoline-1,3(2H)-dione): 6-nitro-imide precursor (200 mg, 0.64 mmol) and excess 2-methoxyethylamine (0.5 mL) in DMF (1 mL) were reacted to yield 33.8 mg (15.5%) of A4 as a bright orange solid. $^1$H NMR (300 MHz, CDCl$_3$) δ 8.59 (d, J=7.5 Hz, 1H, naphthylic-H) 8.46 (d, J=8.7 Hz, 1H, naphthylic-H) 8.13 (d, J=7.5 Hz, 1H, naphthylic-H) 7.63 (t, J=7.8 Hz, 1H, naphthylic-H) 6.72 (d, J=8.7 Hz, 1H, naphthylic-H) 5.66 (br m, 1H, amino-H) 4.32 (t, J=7.2 Hz, 2H, ethylene-CH$_2$) 3.78 (m, J=5.4 Hz, 2H, NHCH$_2$CH$_2$OCH$_3$) 3.58 (m, J=5.4 Hz, 2H, NHCH$_2$CH$_2$OCH$_3$) 3.47 (s, 3H, NHCH$_2$CH$_2$OCH$_3$) 2.65 (t, J=7.2 Hz, 2H, ethylene-CH$_2$) 2.37 (s, 6H, N(CH$_3$)$_2$). Calculated mass for [M+H]$^+$=342.18; observed=342.18.

Synthesis of A5 (6-hexylamino-2-[2-(dimethylamino)ethyl]-1H-benz[de]isoquinoline-1,3(2H)-dione): 6-nitro-imide precursor (200 mg, 0.64 mmol) and excess hexylamine (0.5 mL) in DMF (1 mL) were reacted to yield 81.0 mg (34%) of A5 as a bright orange solid. $^1$H NMR (300 MHz, CDCl$_3$) δ 8.57 (d, J=7.5 Hz, 1H, naphthylic-H) 8.45 (d, J=8.4 Hz, 1H, naphthylic-H) 8.07 (d, J=8.7 Hz, 1H, naphthylic-H) 7.61 (t, J=7.5 Hz, 1H, naphthylic-H) 6.71 (d, J=8.4 Hz, 1H, naphthylic-H) 5.25 (br t, 1H, amino-H) 4.32 (t, J=7.2 Hz, 2H, ethylene-CH$_2$) 3.40 (q, J=7.2 Hz, 2H, NHCH$_2$(CH$_2$)$_4$CH$_3$) 2.66 (t, J=6.9 Hz, 2H, ethylene-CH$_2$) 2.38 (s, 6H, N(CH$_3$)$_2$) 1.81 (m, 2H, hexyl-H) 1.55-1.35 (m, 6H, hexyl-H) 0.93 (t, J=6.9 Hz, 3H, NHCH$_2$(CH$_2$)$_4$CH$_3$). Calculated mass for [M+H]$^+$=368.50; observed=368.0.\

Synthesis of A6 (6-cyclohexylamino-2-[2-(dimethylamino)ethyl]-1H-benz[de]isoquinoline-1,3(2H)-dione): 6-nitro-imide precursor (200 mg, 0.64 mmol) and excess cyclohexylamine (0.5 mL) in DMF (1 mL) were reacted to yield 104 mg (45%) of A6 as a bright orange solid. $^1$H NMR (300 MHz, CDCl$_3$) δ 8.58 (d, J=7.2 Hz, 1H, naphthylic-H) 8.44 (d, J=8.4 Hz, 1H, naphthylic-H) 8.05 (d, J=8.4 Hz, 1H, naphthylic-H) 7.60 (t, J=8.4 Hz, 1H, naphthylic-H) 6.74 (d, J=8.7 Hz, 1H, naphthylic-H) 5.16 (br d, 1H, amino-H) 4.31 (t, J=7.5 Hz, 2H, ethylene-CH$_2$) 3.62 (m, 1H, NHCH-cyclohexyl) 2.65 (t, J=6.3 Hz, 2H, ethylene-CH$_2$) 2.37 (s, 6H, N(CH$_3$)$_2$) 2.19 (m, 2H, cyclohexyl-CH$_2$) 1.90-1.30 (m, 8H, cyclohexyl-CH$_2$). Calculated mass for [M+H]$^+$=366.49; observed=366.0.

Synthesis of A7 (6-piperidinyl-2-[2-(dimethylamino)ethyl]-1H-benz[de]isoquinoline-1,3(2H)-dione): 6-nitro-imide precursor (200 mg, 0.64 mmol) and excess piperidine (0.5 mL) in DMF (1 mL) were reacted to yield 204 mg (91%) of A7 as a bright orange solid. $^1$H NMR (300 MHz, CDCl$_3$) δ 8.57 (dd, J=7.2 Hz, 1H, naphthylic-H) 8.49 (d, J=8.1 Hz, 1H, naphthylic-H) 8.39 (dd, J=8.4 Hz, 1H, naphthylic-H) 7.67 (dd, J=8.4 Hz, 1H, naphthylic-H) 7.17 (d, J=8.1 Hz, 1H, naphthylic-H) 4.32 (t, J=7.2 Hz, 2H, ethylene-CH$_2$) 3.23 (m, 2H, piperidinyl-H) 2.65 (t, J=7.2 Hz, 2H, ethylene-CH$_2$) 2.36 (s, 6H, N(CH$_3$)$_2$) 1.90-1.60 (m, 6H, piperidinyl-H). Calculate mass for [M+H]$^+$=352.20; observed=352.20.

Synthesis of A8 (6-diethylamino-2-[2-(dimethylamino)ethyl]-1H-benz[de]isoquinoline-1,3(2H)-dione): 6-nitro-imide precursor (200 mg, 0.64 mmol) was treated with excess diethylamine (0.5 mL) in DMF (1 mL) to yield 55.6 mg (26%) of A8 as a bright orange solid. $^1$H NMR (300 MHz, CDCl$_3$) δ 8.58 (dd, J=7.2 Hz, 1H, naphthylic-H) 8.49 (d, J=8.4 Hz, 1H, naphthylic-H) 8.45 (dd, J=8.4 Hz, 1H, naphthylic-H) 7.65 (dd, J=8.4 Hz, 1H, naphthylic-H) 7.21 (d, J=8.1 Hz, 1H, naphthylic-H) 4.32 (t, J=7.0 Hz, 2H, ethylene-CH$_2$) 3.41 (q, J=7.2 Hz, 4H, N(CH$_2$CH$_3$)$_2$) 2.66 (t, J=7.0 Hz, 2H, ethylene-CH$_2$) 2.37 (s, 6H, N(CH$_3$)$_2$) 1.68 (t, J=7.2 Hz, 6H, N(CH$_2$CH$_3$)$_2$). Calculated mass for [M+H]$^+$=340.44; observed=340.1.

Synthesis of A9 (2-[2-(dimethylamino)ethyl]-1H-benz[de]isoquinoline-1,3(2H)-dione): This compound was synthesized according to previously published protocols and similar yields and spectral data were obtained [17]. Calculated mass for [M+H]$^+$=269.32; observed=269.3.

NAT2 Assay: This assay was performed using a wild type recombinant human NAT2 (NAT2*4) that was purified from E. coli as previously described [22]. The volume of each reaction was 500 μL with 200 μM amonafide, A1, or A2, 100 μg NAT2*4, and 400 μM AcetylCoA (Sigma-Poole, UK). Reactions were run for 0 or 10 min and stopped by addition of 500 μL of 20% (w/v) trichloroacetic acid (TCA-Sigma-Poole, UK) to give a final TCA concentration of 400 μM, which precipitates the enzyme. Two control assays, lacking either enzyme or compound, were performed for each compound. The reaction mixtures were prepared for analysis by isolation of the compounds from the reaction matrix by solid-phase extraction. In brief, 100 μL of the reaction mixture was added to 1 mL of 2% acetic acid. The sorbent of an Oasis HLB 30 mg Extraction Cartridge (Waters Chromatography—Milford, Mass.) was conditioned with 1 mL of methanol and 1 mL of water, the prepared sample was applied to the conditioned sorbent, and the sorbent was washed with 1 mL of 5% methanol. Samples were eluted with 200 μL methanol followed by 800 μL of 0.1% formic acid in methanol. The eluant was analyzed by an API 3000 LC-MS/MS system (Applied Biosystems—Foster City, Calif.). Samples were infused at 5 μL/min directly into the TurboIonSpray Source (Applied Biosystems—Foster City, Calif.), which was operated in the positive ionization mode. The infusions of all samples were subjected to Q1 scans from 150-600 m/z AMU with unit resolution. Data are represented as the average ratio of the acetylated compound to the parent compound from three separate injections. Reactions with no compound were extracted and injected as well to ensure that there were no peaks in the reaction mixture that corresponded to the masses of amonafide (284.1 m/z), A1 (284.3 m/z), A2 (326.6 m/z), or the acetylated forms (M+42.5 m/z) thereof.

Cell Culture: HeLa (cervical carcinoma), WI-38 (normal human skin fibroblasts), and MDA-MB-231 (breast carcinoma), cells were cultured in DMEM (Invitrogen—Carlsbad, Calif.) and PC-3M (metastatic prostate carcinoma) cells were cultured in RPMI-1640. Peripheral blood mononuclear cells (PBMCs) were voluntarily collected from a healthy laboratory worker by standard sterile phlebotomy techniques and isolated using Vacutainer CPT collection tubes (BD Biosciences—Bedford, Mass.). PBMCs were isolated freshly for each experiment. All DMEM and RPMI-1640 media was supplemented with 10% FBS (Atlanta Biologicals—Lawrenceville, Ga.) and 100 U/mL penicillin and streptomycin (Invitrogen). HUVEC (Human umbilical vein endothelial cells) were cultured in EGM-2 media with supplements provided in the manufacturers BulletKit (Lonza—Walersville, Md.). All cells were maintained at 37° C. and in a 5% CO$_2$ atmosphere.

Growth Inhibition Assays: HeLa, MDA-MB-231, PC-3M, WI-38, and HUVEC cells were plated at 5,000 cells per well in 96 well plates and allowed to attach for 20 hr (8 hr for HeLa). The media was removed and 198 μL of fresh media was added to each well. Each well was treated with one of 14 doses for each compound ($10^5$ nM, $10^{4.75}$ nM, $10^{4.5}$ nM, . . . $10^{1.75}$ nM) for HeLa cells and on of 8 doses for each compound ($10^5$ nM, $10^{4.66}$ nM, $10^{4.33}$ nM, . . . $10^{2.66}$ nM) for the other cell lines to give a final vehicle concentration of 1% DMSO and media volume of 200 μL. PBMCs were isolated and plated at 100,000 per well in 96 well plates with a volume of 197 μL. They were allowed to settle in the media for 20 hr, at which point 1 μL of 1 mg/mL phytohemagglutinin (Sigma—St. Loius Mo.) in PBS was added to stimulate proliferation (final concentration of 5 μg/mL). Each well was treated with one of 8 doses for each compound ($10^5$ nM, $10^{4.66}$ nM, $10^{4.33}$ nM, . . . $10^{2.66}$ nM) to give a final vehicle concentration of 1% DMSO and media volume of 200 μL. Cell proliferation was measured at t=0

(time at start of treatment) and t=72 hr using MTS AQueous non-radioactive proliferation assay (Promega—Madison, Wis.). This assay utilizes the metabolic conversion of yellow tetrazolium to a purple formazan by live cells and the color change is proportional to the number of cells [23]. For HeLa, MDA-MB-231, PC-3M, WI-38, HUVEC, cells, the media was removed and replaced with 120 µL of 1:5 v/v MTS: media solution and allowed to incubate for 1 hr at 37° C. For PBMCs, 40 µL of the MTS solution was added directly to the media and allowed to incubate for 4 hr at 37° C. The absorbance at 490 nm in each well was read with a Spectramax 250 plate reader (Molecular Devices—Sunnyvale, Calif.). The absorbance at t=0 was subtracted from all absorbances at t=72 hr so that a 100% growth inhibitory concentration ($[GI_{100\%}]$) corresponds to when $abs_{72hr}=abs_{0hr}$. Each experiment was repeated four times and the data for each concentration were averaged and growth inhibition curves were constructed using XLfit4 software (IDBS—Guildford, UK). Data were fit to one site dose response curves in order to obtain specific growth inhibitory concentrations and the relative standard errors of the mean for these concentrations were calculated by the XLfit4 software. Statistical significance (p value) for the selectivity and all subsequent assays was determined with the two tailed homoscedastic Student's t-test. Subsequent assays that utilize the $[GI_{99\%}]$ are 20 hr in duration and assays that utilize the $[GI_{50\%}]$ are 72 hr in duration. GI doses are used in subsequent assays to standardize the effects of the compounds, so that biological responses can be correlated among the different compounds at equitoxic doses.

Figure 3:
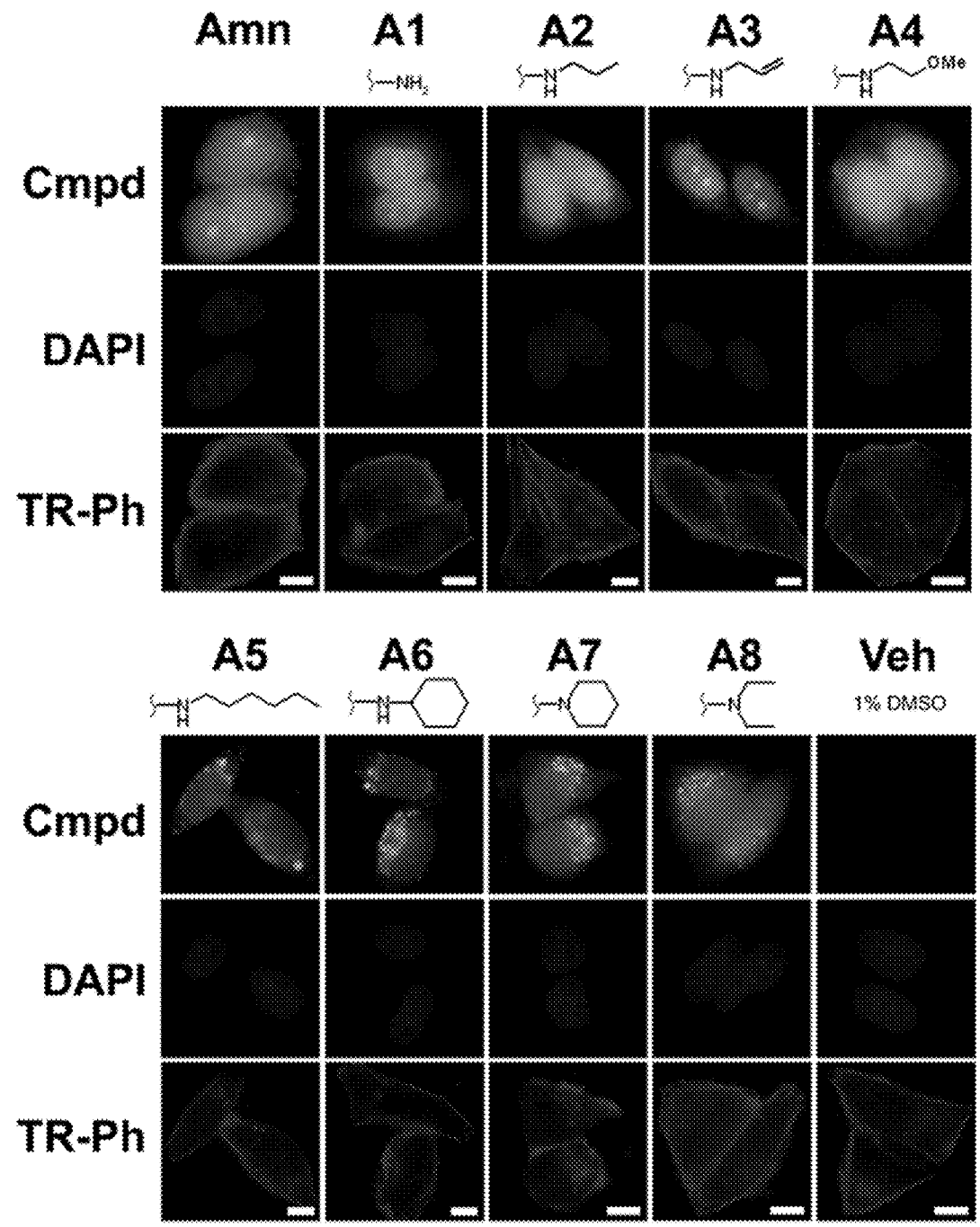
FIG. 3 shows subcellular localization of amonafide (Amn) and A1-A8. These compounds fluoresce in the green channel; therefore, the signal in the first row represents the relative subcellular localization of each compound (Cmpd). The middle row is the DAPI staining to mark the nucleus and the bottom row is Texas Red-Phalloidin (TR-Ph) staining to mark the boundaries of the cytoplasm. The last column is a representative picture of vehicle treated cells (Veh) to show that the signals observed in treated cells are not due to auto-fluorescence of endogenous cellular components. Scale bars=10 µm. The 6-position amino group is shown below each derivative. Differential sub-cellular localization was observed with the more hydrophobic derivatives localizing heavily to cytoplasmic puncta while the others preferentially localize to the nucleus. A9 was included in this figure as it lacks the aryl amine and hence does not fluoresce.

Subcellular Compound Localization: HeLa cells were plated at 250,000 per 35 mm well with a sterile glass coverslip. The cells were allowed to attach for 20 hr and then treated with the $[GI_{99\%}]$ of each derivative 20 hr (total media volume 10 mL/well). The media was removed and the cells were rapidly fixed in 4% w/v paraformaldehyde in PBS for 12 min, permeabilized with 0.5% w/v Triton X-100 in PBS for 5 min, stained with 1.5 mU/µL Texas Red labeled phalloidin (Invitrogen) for 15 min to mark the cytoplasm (F-actin), counterstained with 50 ng/mL DAPI in PBS for 2 min to mark the nuclei (heterochromatin), and then mounted on slides with mounting media (Vector Laboratories—Burlingame, Calif.). The fluorescence of the compounds were detectable in the FITC/GFP channel (490 nm-520 nm emission filter) of a Nikon E800 fluorescent microscope. Images are representative for each compound and were acquired using a 100× objective, SenSys cooled CCD camera (Photometrics—Tucson, Ariz.), and MetaView v 4.5 software (Universal Imaging Corp.—West Chester, Pa.). Scale bars=10 µm. DAPI staining was used to bring the nucleus, including the nucleoli, into focus and this focus plane was used to acquire images in the blue and green channels. The microscope was refocused at the bottom of the cell to acquire images of the phalloidin staining to definitively mark the cytoplasmic boundaries. Images of vehicle treated cells were acquired with the same exposure, brightness, and contrast as compound treated cells to ensure that the signals in the green channel are not due to auto fluorescence of the cells. The vehicle image in FIG. 3 is representative of these images. A9 does not fluoresce, hence was excluded from this assay.

DNA Intercalation Assay: A DNA unwinding assay was performed as previously described [1] with minor modifications. Four Units of recombinant wild type human topoisomerase I (Topogen—Port Orange, Fla.) were incubated with reaction buffer (included with enzyme), ~0.5 µg of pBR322 plasmid DNA, which is a mixture of form I and form II plasmid DNA, and water added to a final volume of 19 µL. The reactions were incubated at 37° C. for 30 min and then 1 µL of each compound was added to give a final concentration of 10, 31.6, and 100 µM (final solvent concentration of 1% DMSO) and the reaction mixture was incubated at 37° C. for another 30 min. The reaction was stopped by the addition of 5 µL gel loading dye [1]. The samples were immediately loaded onto a 1% agarose gel and electrophoresis was performed at 50 V for 3 h at room temperature. Pictures of the gels were obtained using a Kodak Image Station 440 CF (Kodak—Rochester, N.Y.) equipped with a UV source.

In Vitro Topoisomerase Inhibition: HeLa cells were plated at a density of 1.5 million in 35 mm wells and allowed to attach for 20 hr. They were then treated with each compound at the $[GI_{99\%}]$ in 10 mL media for 20 hr. In vitro topoisomerase II inhibition was quantified using TopoGEN's Topoisomerase II In vivo Link Kit according to the protocol included with the kit and according to a previously published protocol [24] with slight modifications. In summary, DNA was isolated from sarkosyl lysed cells, layered on a cesium chloride gradient (total volume ~7 mL), ultra-centrifuged, and then fractionated to 0.5 mL. The fractions were diluted 1:4 v/v in PBS and the fractions containing the genomic DNA were determined by measuring the absorbance at 260 nm for each fraction. The fractions were then loaded into a slot blotting apparatus and pulled through a nitrocellulose membrane by vacuum. The membrane was blocked in 5% w/v milk in 1×TBST (blotto) for 2 hr, incubated in 1:5,000 v/v topoisomerase II (topo II) primary antibody (TopoGEN) in blotto for 1 hr, washed, and incubated in 1:2,000 v/v HRP conjugated anti-rabbit secondary antibody (Jackson—West Grove, Pa.) in blotto for 45 min, washed and developed with SuperSignal West Pico Chemiluminescent Substrate (Pierce—Rockford, Ill.). The data were processed by dividing the intensity of the 2 or 3 most intense topo II immuno-reactive bands by the amount of DNA in the respective fractions. The band intensity was determined by scanning the developed films with a Kodak Image Station 440 CF and measuring the average pixel intensity of an area slightly larger than each band and subtracting the median background pixel intensity of the perimeter of the same area using Kodak MI software. Etoposide (TopoGEN) and mitoxantrone (Sigma—St. Louis, Mo.) are topo II inhibitors used as positive controls. Camptothecin (Sigma—St. Louis, Mo.) is a selective topoisomerase I inhibitor and was used as negative control. Data were standardized to mitoxantrone in each of three independent experiments.

DNA Damage Response Assay: 250,000 HeLa cells were plated in 35 mm culture dishes and allowed to attach for 8 hr and were then treated with the $[GI_{99\%}]$ of each compound for 20 hr (total media volume was 10 mL/well with 1% DMSO). After treatment cells were lysed in 150 µL detergent buffer containing 1:100 v/v protease inhibitor cocktail (Sigma—St. Louis, Mo.). Lysates were run on denaturing 12% acrylamide gels and transferred to nitrocellulose membranes. The membranes were blocked in blotto, incubated in anti-pThr68-Chk2 antibody (Cell Signaling—Danvers, Mass.) at 1:500 v/v dilution in blotto overnight 4° C., washed, incubated in HRP conjugated anti-rabbit secondary antibody (Jackson) at 1:5,000 v/v dilution in blotto for 1 hr, and then developed. The membranes were then stripped with a reducing buffer, blocked in blotto, incubated in anti-Chk2 antibody (Biolegend—San Diego, Calif.) at 1:500 v/v dilution in blotto overnight at 4° C., washed, incubated in HRP conjugated anti-mouse secondary antibody (Jackson) at 1:5, 000 v/v dilution in blotto for 1 hr, and then developed. Membranes were developed with PicoWest Developing Solution (Pierce) and exposed to film. The intensities of bands were quantified as described in the previous section. The data are expressed as the average ratio of pThr68-Chk2 to total Chk2 as normalized to the mitoxantrone control in each of three independent experiments.

Transwell Invasion Assay: HeLa cells were plated at 250,000 per 35 mm well and allowed to attach for 8 hr. The cells were washed with PBS and then treated for 4 hr with the [$GI_{99\%}$] of each compound (or 1% DMSO—vehicle control) in serum free media to decrease the number of invading cells in the beginning of the experiment due to a preliminary lack of drug exposure. The cells were then trypsinized and counted by trypan blue exclusion with a hemacytometer (Sigma—St. Louis, Mo.). Eight micron pore size control well inserts for 12 well plates (BD Biosciences) were coated with 100 µL 1 mg/mL matrigel (Sigma—St. Louis, Mo.) and allowed to solidify at room temperature for 1 hr. The excess matrigel was aspirated and the inserts were gently washed with PBS. The cells were seeded at a density of 300,000 per insert well in a volume of 500 µL serum free media containing a derivative or vehicle. The inserts were then placed in wells containing 700 µL serum free media with the respective compound. After 20 hr the cells on the top of the membranes were gently removed with a cotton swab, the membranes then were fixed in methanol for 1 min, stained in Gills No. 3 Hematoxylin (Sigma—St. Louis, Mo.) for 5 min, rinsed in tap water, and allowed to dry overnight. The membranes were excised, mounted on slides, and the cells were counted under the 40× objective of a bright field microscope. The data are expressed as the average total number of invading cells counted in 20 fields of each membrane, as standardized to the vehicle control, from six experiments.

Perinucleolar Compartment (PNC) Reduction: HeLa cells (PNC prevalence ~85%) were plated 5,000/well in glass bottom 96 well plates and allowed to attach for 8 hr. The cells were then treated with compounds at the respective [$GI_{50\%}$] for 72 hr and [$GI_{99\%}$] for 20 hr for each compound (total media volume was 200 µL/well with 1% DMSO). After treatment cells were immunofluorescently stained as previously described [28], but with a Texas Red labeled secondary antibody (Jackson) instead of a FITC labeled secondary antibody. PNC prevalence (% of non-apoptotic/non-mitotic cells with 1 or more PNCs) was determined by scoring >200 cells per well with fluorescent microscope (60× objective) and images were acquired with the digital camera and image acquisition software previously mentioned. Scale bar=10 µm. Data are expressed as the average PNC prevalence (% control) of three individual experiments.

Results and Discussion

Chemical synthesis of derivatives: In experiments conducted during the course of development of embodiments for the present invention, derivatives of amonafide that cannot be metabolized by NAT2 (FIG. 1A) while retaining biological activity to potentially dose patients with an amonafide derivative independent of NAT2 genotype or phenotype were developed. Amonafide derivatives with free or protected amines at the 6-position, instead of the 5-position of amonafide, were created. Amino derivatives at the 6-position were synthesized for several reasons including, but not limited to, 1) the chemical synthesis of most derivatives (A2-A8) had not been described, 2) they are chemically very similar to amonafide compared to previously reported derivatives such as mitonafide, azonafide, and elinafide, which do not have aryl amines, and 3) the anti-cancer properties of these molecules have not been described. The derivatives synthesized were chosen because alkylation of the aryl amine will prevent NAT2 acetylation and also to explore the effects of hydrophobicity and primary vs. secondary vs. tertiary aryl amines on the biological activity of this class of compounds. A derivative completely lacking the aryl amine (A9) was also synthesized as a control to determine the biological significance of the aryl amine. The synthesis of A1-A9 was relatively simple and rapid. All reactions were 1 or 2 steps from commercial reactants to final product. The hydrogenation of the 6-nitro-imide precursor to produce A1 was the most efficient reaction at 99%, while the yield for A2-A9 is between 16%-91% (FIG. 1B). This ease of synthesis will allow for rapid synthesis of follow up derivatives in the future if needed.

NAT2 metabolism of derivatives: To determine if the novel derivatives are substrates for NAT2, a NAT2 assay was performed that has been previously described [22]. NAT2*4, a rapid acetylating wild type recombinant protein [22], was used in solution with its coenzyme, acetylCoA, to determine if it can acetylate amonafide (positive control), A1 (derivative with a free amine), and A2 (representative negative control with a chemically substituted, or "blocked," aryl amine). The reaction mixtures were incubated for 10 minutes, stopped, solid phase extracted, and then injected into a mass spectrometer to determine the extent of N-acetylation. Amonafide underwent extensive acetylation while A2, which lacks the free amine necessary for NAT2 activity, was not acetylated (FIG. 1C). A1 was very minimally acetylated compared to amonafide, demonstrating that simply moving the aryl amine to the 6-position successfully blocks the acetylation of this chemotype. This finding could be explained, for example, by the aryl amine at the 6-position being less sterically favorable for acetylation in the enzymatic pocket, or by the free amine at the 6-position being less nucleophilic than an amine at the 5-position, or due to a combination of both factors. In some embodiments, as the compounds of the present invention have chemical similarity with amonafide and an inability to be acetylated by NAT2, the present invention contemplates that these derivatives may be developed as potential replacements for amonafide or as novel anti-cancer drugs that are not metabolized by NAT2.

Figure 2:
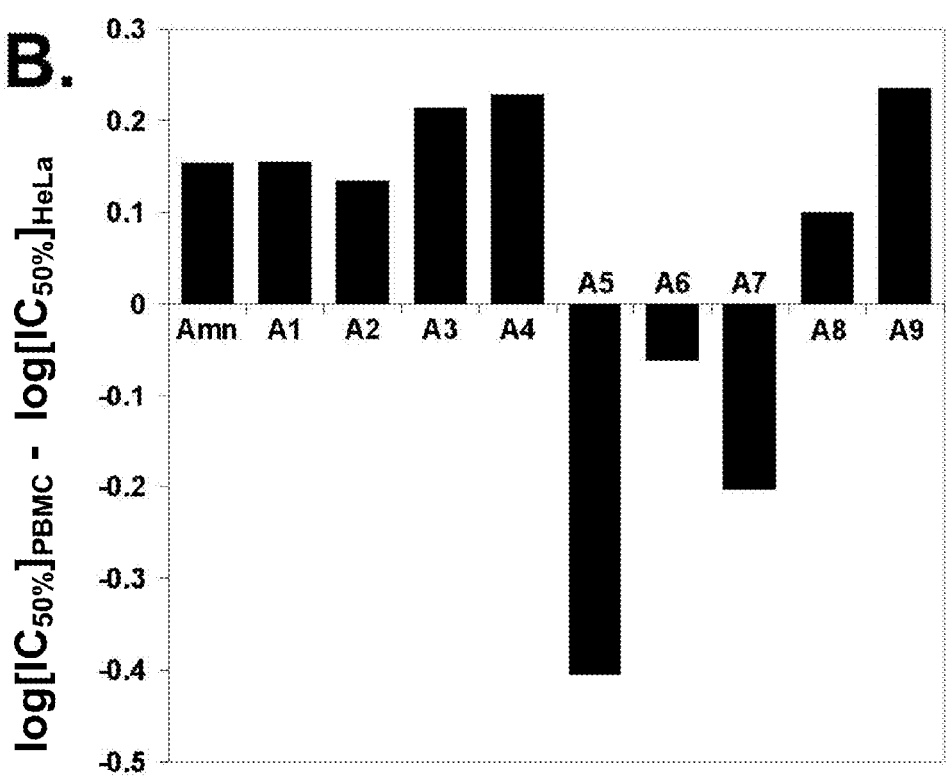
FIG. 2 shows potencies and selectivity indicies of amonafide and derivatives. (A) Growth inhibition potencies of amonafide and A1-A9 against HeLa cells and PBMCs as determined by the MTS proliferation assay. 6-position amino composition or presence is minimally important for potencies in cultured cells. (B) Selectivity indices for the same compounds. The selectivity was calculated according to the formula on the y-axis so that a positive value corresponds to selective growth inhibition of HeLa cells over PBMCs. The composition of the 6-position amino group does affect the selectivity of these compounds.

Growth inhibition and cancer cell selectivity: Derivatives to be considered as potential replacements for amonafide may have, for example, similar or better anti-cancer activities than amonafide. Therefore the in vitro activities of A1-A9 compared to amonafide by constructing growth inhibition curves for three human cancer cell lines (HeLa, PC-3M, and MDA-MB-231) was first characterized. The potencies of the derivatives were not greatly affected by the chemical alterations at the 6-position (FIG. 2). A9 still remains fairly potent even though it completely lacks an aryl amine, which demonstrates, for example, the aryl amine is not a necessary molecular feature for growth inhibition in cell lines; however, the derivatives with a primary or secondary amine are the most potent. These data, along with the known metabolic inactivation of amonafide in humans [13] (FIG. 1A) and previously reported in vivo potencies of 5-amino derivatives [17], support that, for example, the dimethylamino group of the molecule is the most active pharmacophore for growth inhibitory activities. However, the chemical composition of the amine in the 6-position can affect the selectivity of these compounds. Normal cells (PBMC, HUVEC, and WI-38) were treated with A1-A9 and amonafide to construct GI curves so the cancer cell selective growth inhibition of the derivatives could be compared to amonafide (FIG. 2). PBMCs were chosen as normal cells since the major toxicities associated with amonafide in clinical trials were hematological [4-6, 9] and the other cell lines were chosen since they are non-transformed normal primary endothelial and fibroblastic human cells. Amonafide and most derivatives are slightly more potent (but not with statistical significance) or equally potent at inhibiting the growth of cancer cells over normal cells. However, the most hydrophobic derivatives (A5-A7) are preferentially inhibiting the growth of normal cells with A5 doing so significantly ($p<0.05$), which suggests, for example, that these compounds would not be suitable for further development as anti-cancer drugs (FIG. 2B). In summary, the in vitro potencies of 2-[2-(dimethylamino)ethyl]1H-Benz[de]isoquinoline-1,3(2H)-diones are not greatly affected by the presence of, or chemical alterations of, a 6-position aryl amine; however, the selectivity can be altered by the presence and composition of the amino group in the 6-position.

Subcellular localization of derivatives: Previous studies have shown differential, side-chain dependent, subcellular localization with azonafide derivatives [18, 26], so it was determined if chemical alterations at the aryl amine may change subcellular localization of the 6-amino derivatives, which can potentially affect the biological actions of these compounds. The fluorescence of these compounds can be detected in the green channel (490-520 nm emission filter) of a fluorescent microscope, with exception of A9, which does not fluoresce. Therefore, the subcellular localization of these compounds in treated and fixed HeLa cells by epifluorescence microscopy was able to be determined. The nucleus and cytoplasm were stained to show the relative distribution of the compounds within cells (FIG. 3A). All of the compounds localize to the nucleus to some extent, but the hydrophobic derivatives (A5-A8) appear to localize predominantly in cytoplasmic puncta (FIG. 3). The more hydrophilic compounds (amonafide and A1-A4) localize predominantly to the nucleus, with amonafide, A3, and A4 preferentially localizing to the nucleolus over the nucleoplasm. Subcellular localization patterns do not seem to correlate with the selectivity or potency observed for these compounds. Based on the intensity of the fluorescence observed by epifluorescent microscopy and based on the yellow hue (color of amonafide and A1-A8 in solution) of cells observed by bright field microscopy, cells treated with the hydrophobic derivatives (A5-A8) attained much higher cellular concentrations at equitoxic doses. The large cellular build up and poor selectivity of the hydrophobic derivatives (A5-A8) indicate that they may not be as efficacious in vivo as they would likely require large doses and hence may cause many side effects prior to exerting anti-tumor effects.

Figure 4:
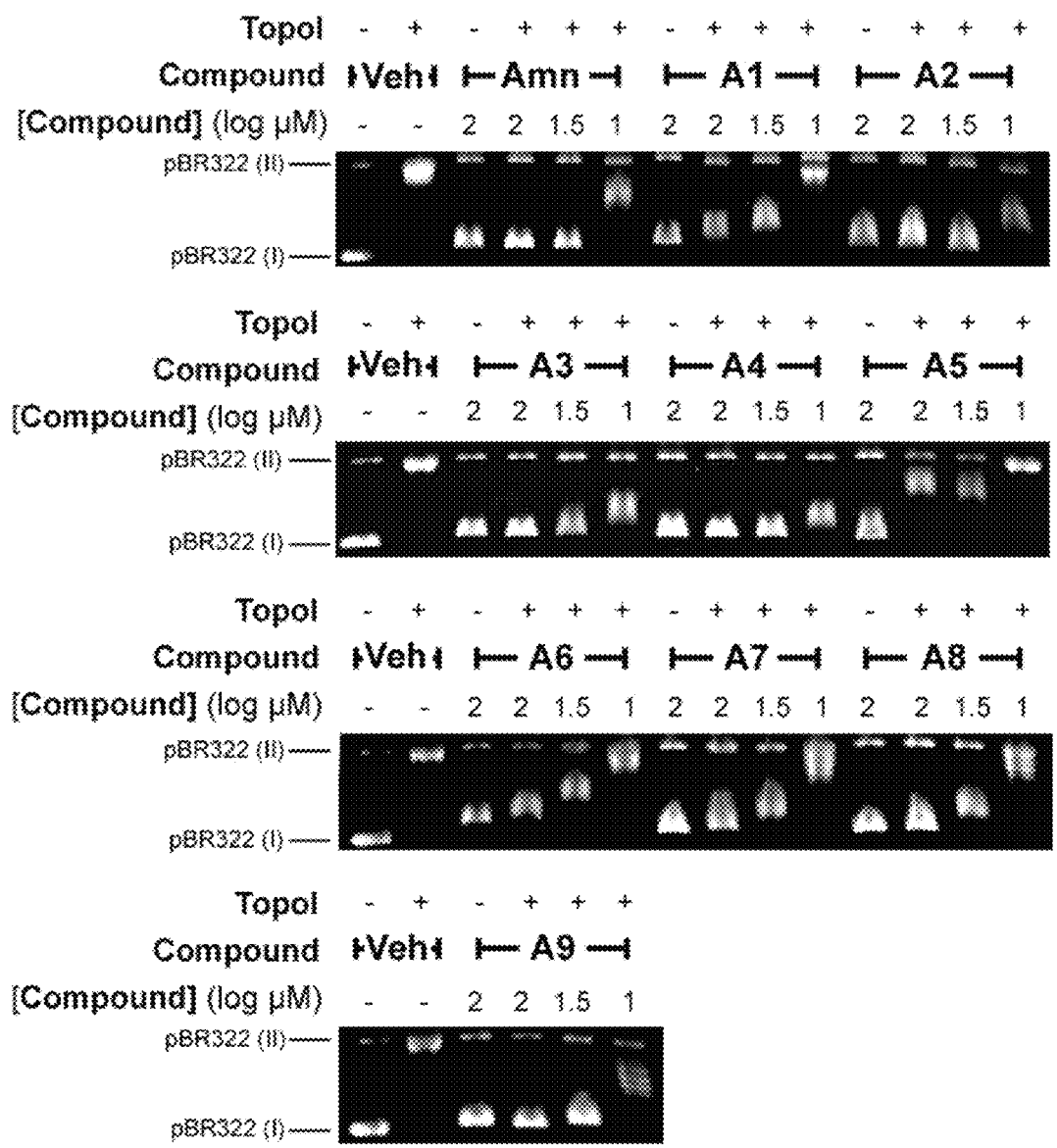
FIG. 4 shows DNA intercalation assay data. pBR322DNA was incubated with various concentrations of each derivative or vehicle (1% DMSO) and toposiomerasel (or water) was added to each reaction. The topoI enzyme cannot relax DNA that is unwound by an intercalating agent. Therefore, compounds that intercalate DNA shift the equilibrium of the reaction towards form I pBR322. A1 and the hydrophobic derivatives (A5-A8) intercalated DNA to a lesser extent than amonafide and the other derivatives.

DNA intercalation: Amonafide and its structural analogs have been shown to cause topoisomerase II (topo II) dependent DNA damage in purified systems [1, 3]. This activity depends on the ability of these compounds to intercalate DNA, which is the proposed mechanism of cytotoxic action of amonafide and its analogs [1, 3]. Therefore, the intercalation of plasmid DNA by A1-A9 was compared with the intercalation by amonafide to determine if they behave similarly. A topoisomerase I (topo I) based plasmid DNA unwinding assay was used to determine the intercalation of each compound [1]. If a DNA intercalating agent is added to this reaction, topo I cannot relax the DNA since the DNA writhe will be altered, leading to an equilibrium that favors the form I (supercoiled) DNA. The results of this assay indicated that all derivatives (A1-A9) indeed intercalate DNA; however, A5 intercalates much less than the other compounds, followed by the other hydrophobic derivatives (A6-A8) and A1 (FIG. 4). When topo I is absent from the reaction the DNA band is slightly shifted up on the gel, further supporting that these compounds are intercalating DNA.

Figure 5A:
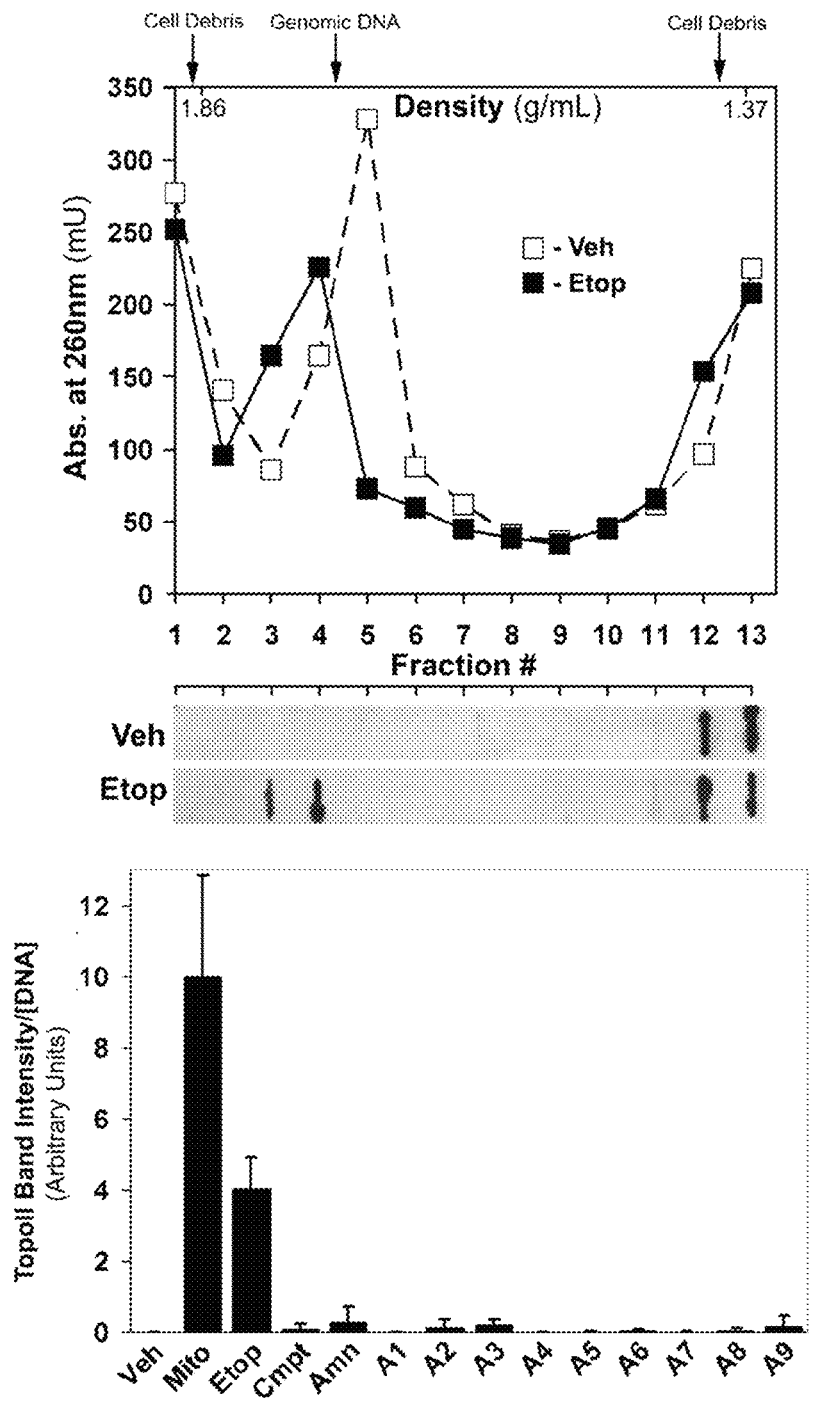
FIG. 5 shows in vivo topoisomeraseII inhibition assays. (A) Top panel: Example of fractionation and spectrometry to isolate genomic DNA and the correlating slot blot for detection of topoII-DNA crosslinks using a positive (etoposide) and a negative (vehicle—1% DMSO) control. Bottom panel: Quantification of topoII-DNA complexes in HeLa cells treated with 1% DMSO (Veh) or [$IC_{99\%}$] of mitoxantrone (Mito—1.01 µM), etoposide (Etop—9.62 µM), camptothecin (Cmpt—280 nM), amonafide (Amn), and amonafide derivatives (A1-A9). Error bars=+SD. Amonafide and A1-A9 do not stabilized topoII-DNA cleavable complexes like other topoII inhibitors. (B) Quantification of DNA damage response in HeLa cells treated with the [$IC_{99\%}$] by western blotting for phospho-Thr68 Chk2 and total Chk2 protein as a surrogate marker of in vivo topoII inhibition. The ratio of activated Chk2 was determined by dividing the intensity of the p-Chk2 bands by the intensity of the Chk2 bands (error bars=SD). Differential DNA damage response was observed among the derivatives. Data from (A) and (B) experiments were normalized to the response of mitoxantrone.

Topoisomerase II inhibition: Amonafide, mitonafide, and azonafide have been all been shown to cause protein linked DNA breaks in vitro [1, 18], which is considered an indicator of topoisomerase inhibition. However, the mechanism by which these compounds inhibit topo-II is not clear. The cytotoxic mechanism of action of most clinically used topo II inhibitors is stabilization of topo II-DNA cleavable complexes. These complexes can be detected in treated cells after genomic DNA extraction [24] and detection of such cleavable complexes more directly indicates topo II inhibition than detecting general DNA-protein links. Therefore, an in vitro topo II inhibition assay was utilized, which detects such topo II-DNA cleavable complexes (FIG. 5A) in order to determine if amonafide or A1-A9 inhibit topo II by stabilizing the cleavable complex. In this assay cells are treated with compounds for 20 hours and then lysed to obtain the genomic DNA, and finally the DNA is blotted with topo II antibodies to determine if any topo II complexes are associated with the DNA. The positive control compounds, mitoxantrone and etoposide, caused formation of abundant drug stabilized topo II-DNA cleavable complexes in HeLa cells (FIG. 5A). Camptothecin (a selective topo I inhibitor) was a negative control and did not cause the stabilization of topo II-DNA cleavable complexes (FIG. 5A). The results show that amonafide and A1-A9 treated cells produced very little to no detectable stabilized topo II-DNA cleavable complexes (FIG. 5A). These results suggest, for example, that amonafide, and structurally related derivatives, do not inhibit topo II in cells by the same mechanism as other topo II inhibitors. The results are consistent with the past finding that amonafide is an ATP-independent inhibitor of topo II, in contrast with other well characterized and clinically used topo II inhibitors, which are ATP-dependent [25]. These findings suggest, for example, that topo II inhibition by amonafide and it derivatives is likely a consequence of the DNA intercalation, but not due to direct inhibition of the topo II enzyme itself. Perhaps the intercalation by this class of compounds stabilizes the DNA breaks caused by topo II so they can not be religated, but does not trap the enzyme on the DNA.

Figure 5B:
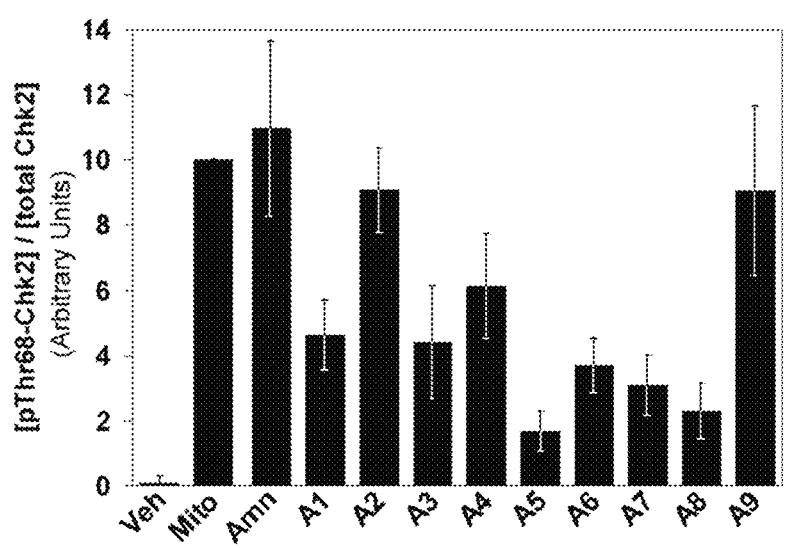

Topoisomerase inhibition by most mechanisms should cause activation of DNA damage response pathways because of the production of single and double strand DNA breaks, as is the case with amonafide [3]. It is reasonable to expect that A1-A9 are causing the same type of DNA damage as amonafide since the dimethylamino-imide is the most active pharmacophore of the amonafide molecule [1] and since this pharmacophore is consistent among the derivatives. Therefore, measuring the DNA damage response at a fixed cytotoxic dose ($[GI_{99\%}]$) will determine the extent that DNA damage contributes to the cytotoxicity of these compounds. Phosphorylation of Chk2 at threonine-68 (Thr68) is an upstream DNA damage response signaling event, subsequent to the activation of ATR/ATM kinases, which are direct responders to DNA damage by inhibiting the cell cycle [27]. Activation of Chk2 was determined by measuring the ratio of pThr68-Chk2 to total Chk2 in HeLa cells treated with the $[GI_{99\%}]$. Amonafide, A2, and A9 evoked the strongest DNA damage response while the most hydrophobic derivatives (A5-A8) caused the least DNA damage response compared to amonafide ($p<0.1$, FIG. 5B). This data qualitatively correlates with the performance of these compounds in the DNA intercalation assay, which supports the hypothesis that topo II inhibition by these compounds is a result of DNA intercalation rather than direct inhibition of topo II.

The differential DNA damage response among the derivatives suggests, for example, that these compounds may have off-target mechanisms of action or differential downstream affects. The cytoplasmic localization of the hydrophobic derivatives (A5-A8) suggests, for example, these compounds likely have cytotoxic mechanisms of action other than DNA intercalation. Amonafide derivatives, for example, likely bind differential DNA sequences, leading to differential biological impacts. For example, some compounds may preferentially bind gene rich sequences that are important for cell proliferation and thereby alter the transcription of these genes, leading to a reduction in cellular proliferation. While other derivatives may inhibit cell growth mainly through the activation of the DNA damage response pathways, such as Chk2 activation, which inhibit the cell cycle. It is likely, for example, that the derivatives inhibit cell growth through differential combinations of these two mechanisms or by other mechanisms.

Figure 6:
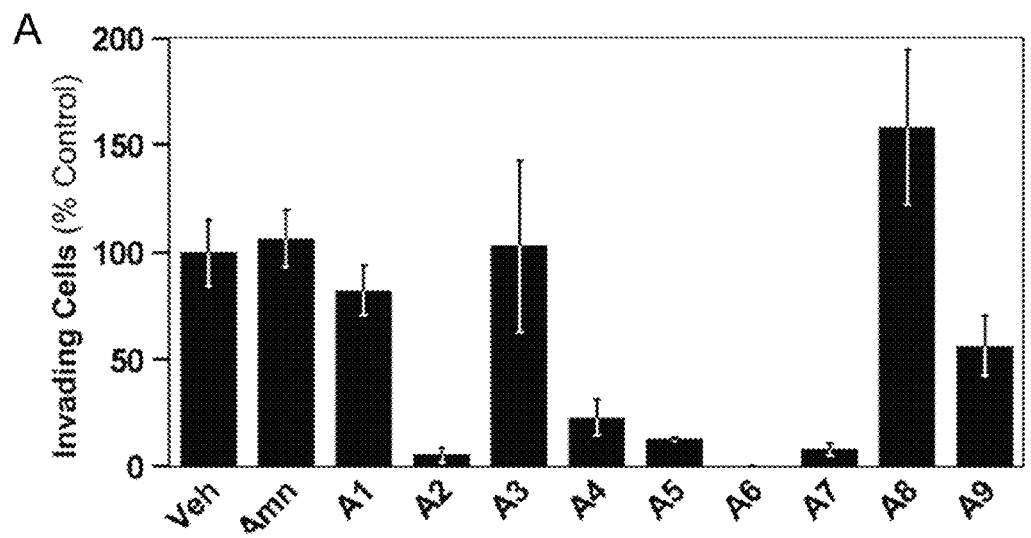
FIG. 6 shows the effect of amonafide and A1-A9 on malignant behavior. (A) Transwell invasion assay quantification to measure the anti-metastatic ability of the derivatives. Data were normalized to % invading cells as compared to the vehicle (1% DMSO) control (error bars=SD). (B) Top panel: HeLa cells treated with 1% DMSO (Veh) or 8.26 µM amonafide (Amn) for 20 hr and then immunofluorescently stained with antibodies to PTB (a component of the PNC).
Figure 6:
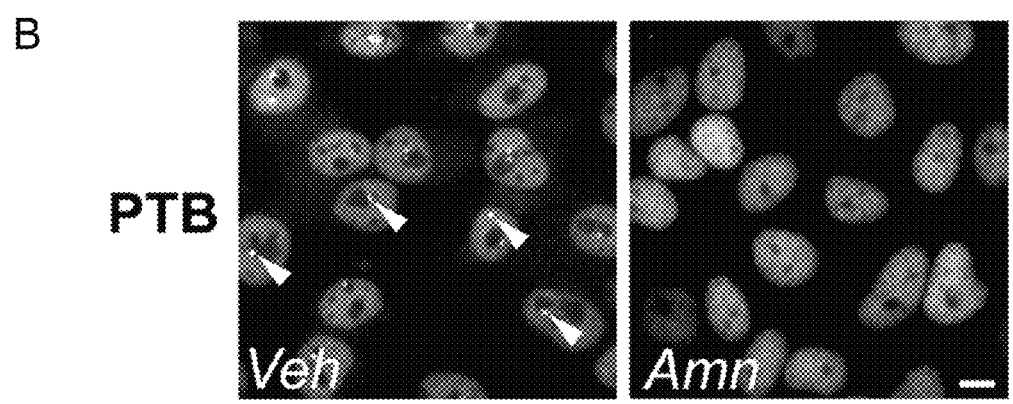
Figure 6:
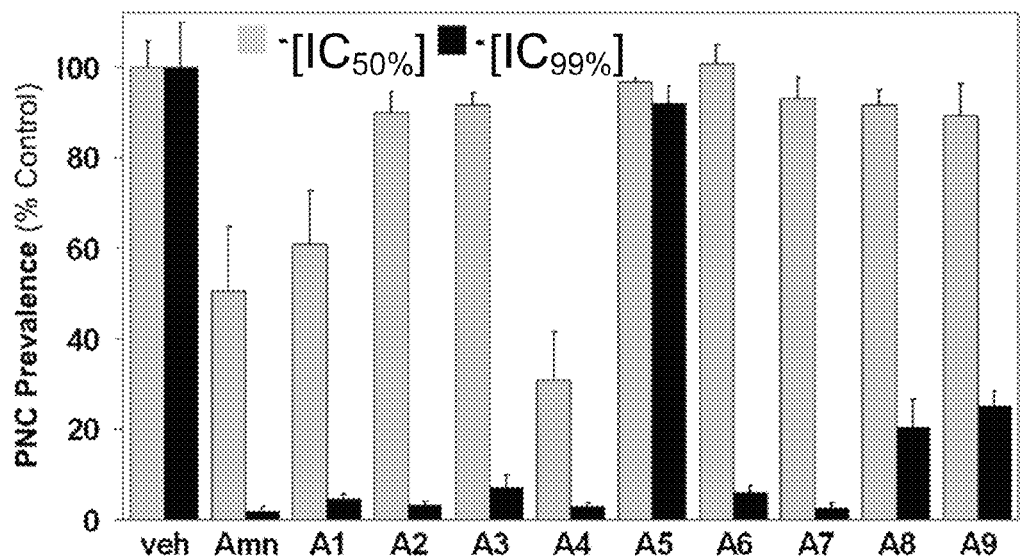

Effect of derivatives on the malignant phenotype—invasion assay: If A1-A9 have differential targets, DNA binding specificity, or downstream effects they may differentially alter the malignant behavior of cells. Also, anti-cancer compounds can be efficacious against tumors in other ways besides inhibiting growth and inducing death of cancer cells; they can also alter the behavior of malignant cells. Therefore, the ability of A1-A9 and amonafide to alter the invasive behavior of cancer cells in a transwell (also known as Boyden chamber) invasion assay was evaluated, which determines the ability of cells to migrate through a proteinacious gel. This behavior is considered to be representative of cancer cell invasion through the basement membrane of the primary tumor environment. In this assay, treated cells are seeded on to the top of the matrigel-coated porous membrane, allowed to invade through the proteinacious gel onto the underside of the membrane, and then counted. Amonafide, A1, A3, and A8 did not significantly alter the invasive behavior of HeLa cells compared to the control, while the other derivatives significantly (p<0.05) decreased the invasiveness of HeLa cells to varying extents (FIG. 6A). The anti-invasive properties of these compounds show no obvious correlations between any of the other data presented here, which demonstrates, for example, that these compounds are differentially affecting cellular behavior and further suggests, for example, these derivatives have differential off target or downstream effects.

Effect of derivatives on the malignant phenotype—PNC prevalence reduction: It was discovered that amonafide was able to eliminate a phenotypic marker of metastatic cells, called the perinucleolar compartment (PNC). The PNC is a unique structural marker that it is only found in malignantly transformed cancer cells, irrespective of tissue origin, and indicates cells that are capable of metastasis [28-30]. This suggests, for example, that the PNC is a more comprehensive marker of malignancy than currently used molecular markers of malignancy, which are often cancer type specific and not directly involved in promoting the malignant behavior. Previous studies indicate that the PNC likely conveys a functional metastatic advantage to cancer cells [28-30]. The PNC prevalence (% of cells with one or more PNC) in human breast cancer positively correlates with the progression of the disease and is always near 100% in distant metastases [30]. This suggests, for example, that PNC elimination may contribute to activity of amonafide against advanced/metastatic breast cancers in clinical trials [4-6]. Therefore, PNC prevalence reduction of amonafide and A1-A9 for was quantified two reasons: 1) to determine which derivatives will likely be effective against advanced/metastatic cancers and 2) to determine if there is differential PNC reducing activity among the derivatives and, if so, determine if it correlates with other biological activities of these compounds. The PNC prevalence reduction was determined for amonafide and A1-A9 at the respective [$GI_{50\%}$] and [$GI_{99\%}$] doses in HeLa cells, which have a high PNC prevalence of ~85%. At the [$GI_{99\%}$] amonafide and all the derivatives, with the exception of A5, were able to greatly reduce the PNC prevalence (FIG. 6B). Amonafide, A1, and A4 were the only compounds that were able effectively reduce the PNC at their [$GI_{50\%}$] doses, which suggests, for example, that A1 and A4 are the most likely to share similar anti-cancer properties of amonafide and potentially have the best efficacy against metastatic cancers. Again, it was found that these derivatives cause differential biological responses at fixed cytotoxic doses, which supports differential targets or downstream affects of these compounds. Also, PNC prevalence reduction does not correlate with DNA intercalation, DNA damage response, or growth inhibition, which demonstrates that PNC elimination by these derivatives is due to specific molecular interactions of the compounds with cellular targets, not simply a side effect of growth inhibition.

A4 is a strong candidate for further development as it has similar potency and selectivity as amonafide, shows near identical sub-cellular localization to amonafide, reduces PNC prevalence to the same extent as amonafide at the [$GI_{50\%}$], and greatly decreases invasion compared to amonafide and control. The PNC prevalence reduction and inhibition of invasive behavior by A4 suggests, for example, this compound may be efficacious against metastatic and advanced tumors. A1 also deserves further development as its potency, selectivity, sub-cellular localization, PNC prevalence reduction, chemical structure, and physio-chemical properties are near identical to amonafide, which suggests, for example, the biodistribution in animals will be very similar. Although originally included in these studies as a control to determine the biological significance of the 5 and 6-position amines, A9 also deserves further consideration for further development since its potency, selectivity, and DNA damage activation are similar to amonafide and since it decreases invasive behavior.

While these 6-amino amonafide derivatives, named here as numonafides, are chemically very similar to amonafide, the small chemical differences between numonafides and amonafide cause differential in vitro biological activities likely due, for example, to differential off-target, DNA binding specifities, or downstream affects. Also, the chemical differences among the derivatives may cause these compounds to become substrates for metabolic enzymes other than NAT2 and CYP1A2 and may differentially affect their biodistribution and clearance in an animal.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

REFERENCES

1 Hsiang Y H, Jiang J B, Liu L F. Topoisomerase II-mediated DNA cleavage by amonafide and its structural analogs. Mol. Pharmacol. 1989; 36: 371-376; herein incorporated by reference in its entirety.

2 De Isabella P, Zunino F, Capranico G. Base sequence determinants of amonafide stimulation of topoisomerase II DNA cleavage. Nucleic Acids Res. 1995; 23: 223-229; herein incorporated by reference in its entirety.

3 Andersson B S, Beran M, Bakic M, Silberman L E, Newman R A, Zwelling L A. In vitro toxicity and DNA cleaving capacity of benzisoquinolinedione (nafidimide; NSC 308847) in human leukemia. Cancer Res. 1987; 47: 1040-1044; herein incorporated by reference in its entirety.

4 Scheithauer W, Dittrich C, Kornek G, Haider K, Linkesch W, Gisslinger H, et al. Phase II study of amonafide in advanced breast cancer. Breast Cancer Res Treat. 1991; 20: 63-67; herein incorporated by reference in its entirety.

5 Kornek G, Raderer M, Depisch D, Haider K, Fazeny B, Dittrich C, Scheithauer W. Amonafide as first-line chemotherapy for metastatic breast cancer. Eur J. Cancer. 1994; 30: 398-400; herein incorporated by reference in its entirety.

6 Costanza M E, Berry D, Henderson I C, Ratain M J, Wu K, Shapiro C, et al. Amonafide: An active agent in the treatment of previously untreated advanced breast cancer—a cancer and leukemia group B study (CALGB 8642). Clin Cancer Res. 1995; 1: 699-704; herein incorporated by reference in its entirety.

7 http://www, separated by, .xanthus.com/products_xanafide.htm; herein incorporated by reference in its entirety.

8 http://www., separated by, chemgenex.com/wt/page/quinamed; herein incorporated by reference in its entirety.

9 Ratain M J, Mick R, Berezin F, Janisch L, Schilsky R L, Williams S F, et al. Paradoxical relationship between acetylator phenotype and amonafide toxicity. Clin Pharmacol Ther. 1991; 50: 573-579; herein incorporated by reference in its entirety.

10 Kreis W, Chan K, Budman D R, Allen S L, Fusco D, Mittelman A, et al. Clinical pharmacokinetics of amonafide (NSC 308847) in 62 patients. Cancer Invest. 1996; 14: 320-327; herein incorporated by reference in its entirety.

11 Innocenti F, Iyer L, Ratain M J. Pharmacogenetics of anticancer agents: lessons from amonafide and irinotecan. Drug Metab Dispos. 2001; 29: 596-600; herein incorporated by reference in its entirety.

12 Taningher M, Malacarne D, Izzotti A, Ugolini D, Parodi S. Drug metabolism polymorphisms as modulators of cancer susceptibility. Mutat Res. 1999; 436: 227-261; herein incorporated by reference in its entirety.

13 Felder T B, McLean M A, Vestal M L, Lu K, Farquhar D, Legha S S, et al. Pharmacokinetics and metabolism of the antitumor drug amonafide (NSC-308847) in humans. Drug Metab Dispos. 1987; 15: 773-778; herein incorporated by reference in its entirety.

14 Ratain M J, Rosner G, Allen S L, Costanza M, Van Echo D A, Henderson I C, et al. Population pharmacodynamic study of amonafide: a Cancer and Leukemia Group B study. J Clin Oncol. 1995; 13: 741-747; herein incorporated by reference in its entirety.

15 Ratain M J, Mick R, Berezin F, Janisch L, Schilsky R L, Vogelzang N J, et al. Phase I study of amonafide dosing based on acetylator phenotype. Cancer Res. 1993; 53: 2304-2308; herein incorporated by reference in its entirety.

16 Mayr C A, Sami S M, Remers W A, Don R T. Identification and characterization of in vitro metabolites of 2-2'-(dimethylamino)ethyl-1,2-dihydro-3H-dibenz-de, h]isoquinoline-1,3-dione. Drug Metab Dispos. 1998; 26:105-109; herein incorporated by reference in its entirety.

17 Braña M F, Sanz A M, Castellano J M, Roldan C M, Roldan C. Synthesis and cytostatic activity of benz(de)iso-quinilin-1,3-diones. Structure activity relationships. Eur J Med Chem—Chimica Therapeutica. 1981; 16: 207-212; herein incorporated by reference in its entirety.

18 Mayr C A, Sami S M, Don R T. In vitro cytotoxicity and DNA damage production in Chinese hamster ovary cells and topoisomerase II inhibition by 2-[2'-(dimethylamino)ethyl]-1,2-dihydro-3H-dibenz[de,h]isoquinoline-1,3-diones with substitutions at the 6 and 7 positions (azonafides). Anticancer Drugs. 1997; 8: 245-256; herein incorporated by reference in its entirety.

19 Braña M F, Castellano J M, Perron D, Maher C, Conlon D, Bousquet P F, et al. Chromophore-Modified Bis-Naphthalimides: Synthesis and Antitumor Activity of Bis-Dibenz[de,h]isoquinoline-1,3-diones. J. Med. Chem. 1997; 40: 449-454; herein incorporated by reference in its entirety.

20 Braña M F, Cacho M, García M A, Pascual-Teresa B, Ramos A, Domínguez M T, Pozuelo J M, et al. New Analogues of Amonafide and Elinafide, Containing Aromatic Heterocycles: Synthesis, Antitumor Activity, Molecular Modeling, and DNA Binding Properties. J. Med. Chem. 2004; 47: 1391-1399; herein incorporated by reference in its entirety.

21 Brana M, Lopez de Arenosa R, Lopez Rodriguez M L, Martinez Sanz Fernandez A. Quantitative structure-toxicity relationships of benzo[d,e]isoquinoline-1,3-diones. Anales de Quimica, Serie C: Quimica Organica y Bioquimica. 1983; 79: 43-46; herein incorporated by reference in its entirety.

22 Kawamura A, Graham J, Mushtaq A, Tsiftsoglou S A, Vath G M, Hanna P E, Wagner C R, Sim E. Eukaryotic arylamine N-acetyltransferase. Investigation of substrate specificity by high-throughput screening Biochem Pharmacol. 2005; 69: 347-359; herein incorporated by reference in its entirety.

23 Cory A H, Owen T C, Barltrop J A, Cory J G. Use of an aqueous soluble tetrazolium/formazan assay for cell growth assays in culture. Cancer Commun. 1991; 7: 207-212; herein incorporated by reference in its entirety.

24 Muller M T, Mehta V B. DNase I hypersensitivity is independent of endogenous topoisomerase II activity during chicken erythrocyte differentiation. Mol Cell Biol. 1988; 8: 3661-3669; herein incorporated by reference in its entirety.

25 Wang H, Mao Y, Zhou N, Hu T, Hsieh T S, Liu L F. Atp-bound topoisomerase ii as a target for antitumor drugs. J Biol. Chem. 2001; 276: 15990-15995; herein incorporated by reference in its entirety.

26 Mayr C A, Sami S M, Remers W A, Don R T. Intracellular localization of 6- and 7-substituted 2-[2'-(dimethylamino)ethyl]-1,2-dihydro-3H-dibenz[de,h]isoquino line- 27 Ahn J, Urist M, Prives C. The Chk2 protein kinase. DNA Repair (Amst). 2004; 3: 1039-1047; herein incorporated by reference in its entirety.

28 Huang S, Deerinck T J, Ellisman M H, Spector D L. The dynamic organization of the perinucleolar compartment in the cell nucleus. J. Cell Biol. 1997; 137: 965-974; herein incorporated by reference in its entirety.

29 Kopp K, Huang S. The perinucleolar compartment and transformation. J Cell Biochem. 2005; 95: 217-225; herein incorporated by reference in its entirety.

30 Kamath R V, Thor A D, Wang C, Edgerton S M, Slusarczyk A, Leary D J, et al. Perinucleolar compartment prevalence has an independent prognostic value for breast cancer. Cancer Res. 2005; 65: 246-253; herein incorporated by reference in its entirety.

We claim:

1. A method of treating a leukemia comprising administering an effective amount of a pharmaceutical preparation

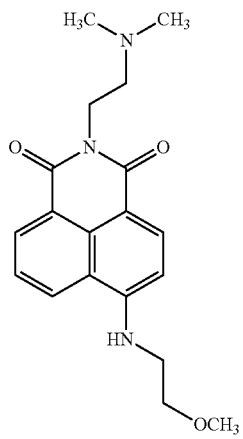 [SMILES: COCCNc1ccc2c3c(cccc13)C(=O)N(CCN(C)C)C2=O]

comprising a pharmaceutical carrier and to a subject in need in thereof.

2. The method of claim 1, further comprising co-administering to said subject an anti-cancer agent.

3. The method of claim 2, wherein said anti-cancer agent is select from the group consisting of Acivicin; Aclarubicin; Acodazole Hydrochloride; Acronine; Adozelesin; Adriamycin; Aldesleukin; Alitretinoin; Allopurinol Sodium; Altretamine; Ambomycin; Ametantrone Acetate; Aminoglutethimide; Amsacrine; Anastrozole; Annonaceous Acetogenins; Anthramycin; Asimicin; Asparaginase; Asperlin; Azacitidine; Azetepa; Azotomycin; Batimastat; Benzodepa; Bexarotene; Bicalutamide; Bisantrene Hydrochloride; Bisnafide Dimesylate; Bizelesin; Bleomycin Sulfate; Brequinar Sodium; Bropirimine; Bullatacin; Busulfan; Cabergoline; Cactinomycin; Calusterone; Caracemide; Carbetimer; Carboplatin; Carmustine; Carubicin Hydrochloride; Carzelesin; Cedefingol; Celecoxib; Chlorambucil; Cirolemycin; Cisplatin; Cladribine; Crisnatol Mesylate; Cyclophosphamide; Cytarabine; Dacarbazine; DACA (N-[2-(Dimethyl-amino)ethyl]acridine-4-carboxamide); Dactinomycin; Daunorubicin Hydrochloride; Daunomycin; Decitabine; Denileukin Diftitox; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Flurocitabine; Fosquidone; Fostriecin Sodium; FK-317; FK-973; FR-66979; FR-900482; Gemcitabine; Geimcitabine Hydrochloride; Gemtuzumab Ozogamicin; Gold Au 198; Goserelin Acetate; Guanacone; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Methoxsalen; Metoprine; Meturedepa; Mitindomide; Mitocarcin; Mitocromin; Mitogillin; Mitomalcin; Mitomycin; Mytomycin C; Mitosper; Mitotane; Mitoxantrone Hydrochloride; Mycophenolic Acid; Nocodazole; Nogalamycin; Oprelvekin; Ormaplatin; Oxisuran; Paclitaxel; Pamidronate Disodium; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rituximab; Rogletimide; Rolliniastatin; Safingol; Safingol Hydrochloride; Samarium/Lexidronam; Semustine; Simtrazene; Sparfosate Sodium; Sparsomycin; Spirogermanium Hydrochloride; Spiromustine; Spiroplatin; Squamocin; Squamotacin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trastuzumab; Trestolone Acetate; Triciribine Phosphate; Trimetrexate; Trimetrexate Glucuronate; Triptorelin; Tubulozole Hydrochloride; Uracil Mustard; Uredepa; Valrubicin; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5, 8-dideazafolic acid; 2-chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlorethamine); cyclophosphamide; melphalan; chlorambucil; ifosfamide; busulfan; N-methyl-N-nitrosourea (MNU); N, N'-Bis(2-chloroethyl)-N-nitrosourea (BCNU); N-(2-chloroethyl)-N'-cyclohex- yl-N-nitrosourea (CCNU); N-(2-chloroethyl)-N'-(trans-4-methylcyclohexyl-N- nitrosourea (MeCCNU); N-(2-chloroethyl)- N'-(diethyl) ethylphosphonate-N-nit- rosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis (platinum); tomudex; azacitidine; cytarabine; gemcitabine; 6-Mercaptopurine; 6-Thioguanine; Hypoxanthine; teniposide; 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl) retinamide; 13-cis retinoic acid; 3-Methyl TTNEB; 9-cis retinoic acid; fludarabine (2-F-ara-AMP); 2-chlorodeoxyadenosine (2-Cda), Antiproliferative agents, Piritrexim Isothionate, Antiprostatic hypertrophy agents, Sitogluside, Benign prostatic hyperplasia therapy agents, Tamsulosin Hydrochloride, Prostate growth inhibitor agents, Pentomone, and Radioactive agents, Fibrinogen I 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m Sulfur Colloid; Technetium Tc 99m Teboroxime; Technetium Tc 99m Tetrofosmin; Technetium Tc 99m Tiatide; Thyroxine I 125; Thyroxine I 131; Tolpovidone I 131; Triolein I 125; and Triolein I 131.

* * * * *

UNITED STATES PATENT AND TRADEMARK OFFICE
CERTIFICATE OF CORRECTION

PATENT NO.        : 9,878,984 B2
APPLICATION NO.   : 14/480235
DATED             : January 30, 2018
INVENTOR(S)       : Sui Huang et al.

Page 1 of 1

It is certified that error appears in the above-identified patent and that said Letters Patent is hereby corrected as shown below:

Column 39, Claim 1 should read:
1. A method of treating a leukemia comprising administering an effective amount of a pharmaceutical preparation comprising a pharmaceutical carrier and

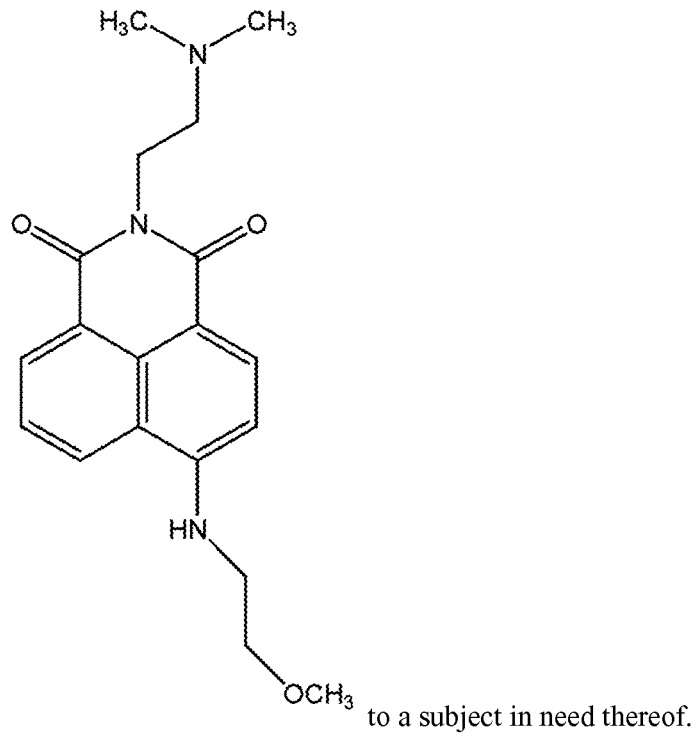

to a subject in need thereof.

Signed and Sealed this
Twenty-ninth Day of May, 2018

Andrei Iancu
*Director of the United States Patent and Trademark Office*